United States Patent
Gerber et al.

(10) Patent No.: US 9,789,307 B2
(45) Date of Patent: Oct. 17, 2017

(54) DUAL PROPHYLACTIC AND ABORTIVE ELECTRICAL STIMULATION

(75) Inventors: Martin T. Gerber, Maple Grove, MN (US); Steven M. Goetz, North Oaks, MN (US); Christopher Poletto, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 644 days.

(21) Appl. No.: 13/456,969

(22) Filed: Apr. 26, 2012

(65) Prior Publication Data

US 2012/0277823 A1    Nov. 1, 2012

Related U.S. Application Data

(60) Provisional application No. 61/480,978, filed on Apr. 29, 2011.

(51) Int. Cl.
*A61N 1/36*    (2006.01)

(52) U.S. Cl.
CPC ........... *A61N 1/36* (2013.01); *A61N 1/36075* (2013.01); *A61N 1/36057* (2013.01); *A61N 1/36082* (2013.01)

(58) Field of Classification Search
USPC ......................................................... 607/46
See application file for complete search history.

(56) References Cited

U.S. PATENT DOCUMENTS

| | | | |
|---|---|---|---|
| 5,306,292 A | 4/1994 | Lindegren | |
| 5,626,629 A | 5/1997 | Faltys et al. | |
| 5,928,272 A | 7/1999 | Adkins et al. | |
| 6,393,325 B1* | 5/2002 | Mann et al. | 607/46 |
| 6,473,644 B1 | 10/2002 | Terry, Jr. et al. | |
| 6,587,724 B2* | 7/2003 | Mann | 607/30 |
| 6,622,048 B1* | 9/2003 | Mann et al. | 607/46 |
| 6,640,136 B1 | 10/2003 | Helland et al. | |
| 6,731,986 B2* | 5/2004 | Mann | 607/30 |
| 7,104,965 B1 | 9/2006 | Jiang et al. | |
| 7,174,215 B2 | 2/2007 | Bradley | |
| 7,254,446 B1 | 8/2007 | Erickson et al. | |
| 7,317,944 B1 | 1/2008 | Overstreet | |
| 7,499,752 B2* | 3/2009 | Maschino et al. | 607/40 |
| 7,519,431 B2* | 4/2009 | Goetz et al. | 607/66 |
| 7,567,840 B2 | 7/2009 | Armstrong | |

(Continued)

FOREIGN PATENT DOCUMENTS

| | | |
|---|---|---|
| EP | 1181951 B1 | 3/2004 |
| WO | 2006073393 A1 | 7/2006 |

(Continued)

OTHER PUBLICATIONS

"Arrhythmia: Heart Palpitations." Cleveland Clinic, http://my.clevelandclinic.org/heart/disorders/electric/palpitations.aspx, captured Mar. 5, 2010.*

(Continued)

*Primary Examiner* — Carl H Layno
*Assistant Examiner* — Erin M Piateski
(74) *Attorney, Agent, or Firm* — Shumaker & Sieffert, P.A.

(57) ABSTRACT

Prophylactic stimulation and abortive electrical stimulation are delivered to a cranial nerve, including, e.g. an occipital or trigeminal nerve to treat symptoms of various conditions, including, e.g. occipital neuralgia or migraines.

27 Claims, 7 Drawing Sheets

(56) References Cited

U.S. PATENT DOCUMENTS

| | | | |
|---|---|---|---|
| 7,578,819 B2 | 8/2009 | Bleich et al. | |
| 7,643,881 B2 | 1/2010 | Armstrong | |
| 7,689,286 B2 | 3/2010 | Pastore et al. | |
| 7,711,419 B2 | 5/2010 | Armstrong et al. | |
| 2002/0072770 A1* | 6/2002 | Pless | 607/2 |
| 2003/0153959 A1 | 8/2003 | Thacker et al. | |
| 2004/0167586 A1 | 8/2004 | Overstreet | |
| 2005/0245987 A1 | 11/2005 | Woods et al. | |
| 2006/0074450 A1 | 4/2006 | Boveja et al. | |
| 2006/0167498 A1* | 7/2006 | DiLorenzo | 607/2 |
| 2006/0173510 A1* | 8/2006 | Besio et al. | 607/45 |
| 2007/0016097 A1 | 1/2007 | Farquhar et al. | |
| 2007/0043395 A1* | 2/2007 | Wei et al. | 607/8 |
| 2007/0233194 A1* | 10/2007 | Craig | 607/2 |
| 2007/0255320 A1 | 11/2007 | Inman et al. | |
| 2008/0086175 A1 | 4/2008 | Libbus et al. | |
| 2008/0147140 A1 | 6/2008 | Ternes et al. | |
| 2008/0269812 A1* | 10/2008 | Gerber et al. | 607/2 |
| 2008/0281381 A1* | 11/2008 | Gerber et al. | 607/62 |
| 2009/0030493 A1 | 1/2009 | Colborn et al. | |
| 2009/0043352 A1 | 2/2009 | Brooke et al. | |
| 2009/0076561 A1 | 3/2009 | Libbus et al. | |
| 2009/0112281 A1* | 4/2009 | Miyazawa et al. | 607/46 |
| 2009/0198294 A1* | 8/2009 | Rossing et al. | 607/4 |
| 2010/0010383 A1 | 1/2010 | Skelton et al. | |
| 2010/0010390 A1 | 1/2010 | Skelton et al. | |
| 2010/0010576 A1 | 1/2010 | Skelton et al. | |
| 2010/0010580 A1 | 1/2010 | Skelton et al. | |
| 2010/0010584 A1 | 1/2010 | Skelton et al. | |
| 2010/0010585 A1 | 1/2010 | Davis et al. | |
| 2010/0010586 A1 | 1/2010 | Skelton et al. | |
| 2010/0030299 A1* | 2/2010 | Covalin | 607/46 |
| 2010/0114192 A1* | 5/2010 | Jaax et al. | 607/3 |
| 2010/0114204 A1 | 5/2010 | Burnes et al. | |
| 2010/0114221 A1 | 5/2010 | Krause et al. | |
| 2010/0121408 A1 | 5/2010 | Imran et al. | |
| 2010/0161007 A1 | 6/2010 | King | |
| 2010/0249875 A1* | 9/2010 | Kishawi et al. | 607/46 |
| 2011/0276107 A1* | 11/2011 | Simon et al. | 607/46 |

FOREIGN PATENT DOCUMENTS

| | | |
|---|---|---|
| WO | 2009134478 A1 | 11/2009 |
| WO | 2009158389 A1 | 12/2009 |
| WO | 2010065146 A1 | 6/2010 |
| WO | 2010105261 A1 | 9/2010 |

OTHER PUBLICATIONS

"Bradycardia (Slow Heart Rate)—Overview". WebMD, http://www.webmd.com/heart-disease/tc/bradycardia-slow-heart-rate-overview, captured Jan. 30, 2010, updated Jun. 18, 2009.*

Schachter et al. "Warning Signs of Seizures", Aug. 2013, [http://www.epilepsy.com/get-help/managing-your-epilepsy/understanding-seizures-and-emergencies/warning-signs-seizures, accessed Sep. 30, 2014].*

U.S. Appl. No. 13/457,063, filed Apr. 26, 2012, entitled "Electrical Stimulation Therapy Based on Head Position,".

U.S. Appl. No. 13/456,829, filed Apr. 26, 2012, entitled "Determining Nerve Location Relative to Electrodes,".

* cited by examiner

DUAL PROPHYLACTIC AND ABORTIVE ELECTRICAL STIMULATION

This application claims the benefit of U.S. Provisional Application No. 61/480,978, filed on Apr. 29, 2011, the entire contents of which is incorporated herein by reference.

TECHNICAL FIELD

This disclosure relates to implantable medical devices.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, migraines, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient.

SUMMARY

In general, the following examples are directed to techniques for treating various patient conditions, including, e.g. occipital neuralgia or migraines by delivering therapy including prophylactic and abortive electrical stimulation modes.

In one example, a method includes delivering prophylactic electrical stimulation to a cranial nerve based on a first range of stimulation thresholds associated with patient perception in the absence of any symptoms of a chronic condition and delivering abortive electrical stimulation to the cranial nerve based on a second range of stimulation thresholds associated with patient perception while a symptom of the chronic condition is occurring. The prophylactic stimulation is configured to inhibit onset of a symptom of the chronic condition. The abortive stimulation is configured to reduce an effect of a symptom of the chronic condition.

In another example, a system includes an implantable electrical stimulation generator and a processor. The processor is configured to control the stimulation generator to deliver prophylactic electrical stimulation to a cranial nerve based on a first range of stimulation thresholds associated with patient perception in the absence of any symptoms of a chronic condition and to deliver abortive electrical stimulation to the cranial nerve based on a second range of stimulation thresholds associated with patient perception while a symptom of the chronic condition is occurring. The prophylactic stimulation is configured to inhibit onset of a symptom of the chronic condition. The abortive stimulation is configured to reduce an effect of a symptom of the chronic condition.

In another example, a computer-readable storage medium includes instructions for causing a programmable processor to deliver prophylactic electrical stimulation to a cranial nerve based on a first range of stimulation thresholds associated with patient perception in the absence of any symptoms of a chronic condition, and deliver abortive electrical stimulation to the cranial nerve based on a second range of stimulation thresholds associated with patient perception while a symptom of the chronic condition is occurring. The prophylactic stimulation is configured to inhibit onset of a symptom of the chronic condition. The abortive stimulation is configured to reduce an effect of a symptom of the chronic condition.

The details of one or more examples are set forth in the accompanying drawings and the description below. Other features, objects, and advantages of examples in accordance with this disclosure will be apparent from the description and drawings, and from the claims.

DETAILED DESCRIPTION

Figure 1A:
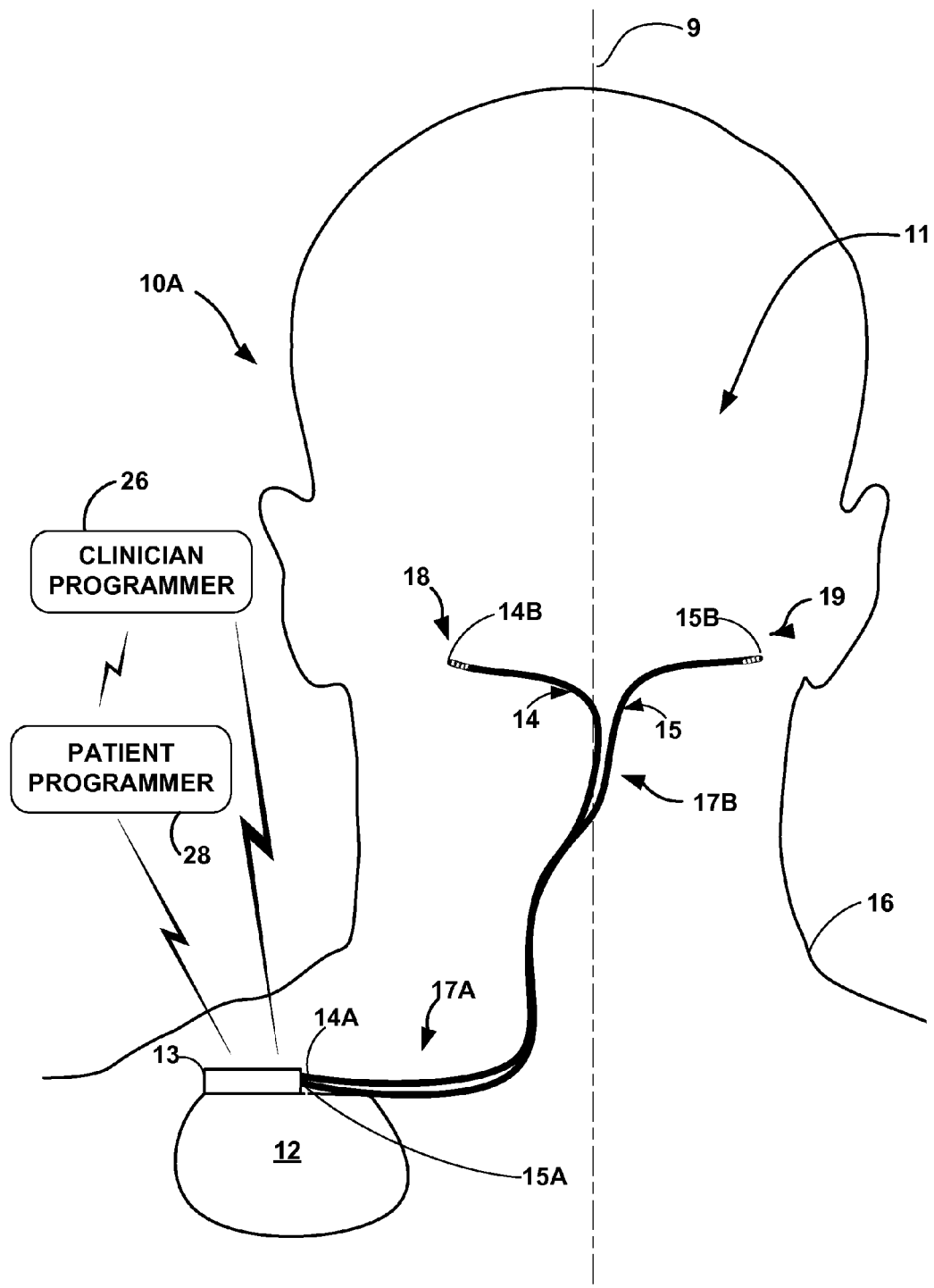
FIG. 1A is a conceptual diagram illustrating an example therapy system that includes an implantable stimulator coupled to an implantable stimulation lead.

Implantable medical devices (IMDs), including, e.g. electrical stimulation devices, commonly include the actual implantable device, including, e.g., a housing containing a battery, device circuitry, and a pulse generator, and a therapy delivery component, e.g. a stimulation lead carrying one or more electrodes by which therapy is delivered to a point of interest within a patient. After an IMD and an associated lead or leads have been implanted within a patient, the IMD may be programmed before the patient begins receiving chronic stimulation therapy for one or more conditions for which the device has been implanted. Programming electrical stimulation therapy generally includes testing stimulation configured according to different electrode combinations and stimulation parameters to determine which electrodes and parameter values deliver the most efficacious therapy to a particular patient. Example stimulation parameters by which stimulation delivered via one or more electrodes may be defined include stimulation amplitude (e.g. current or voltage), pulse width, and frequency. Additionally, in examples including multiple leads arranged in multiple locations, different combinations of leads may be employed in different stimulation therapies. In some cases, efficacious electrode combinations and parameters will be defined as a stimulation program by which therapy may be delivered to the patient after the programming session is concluded. A programming session may yield multiple efficacious stimulation programs, which may remain separate or which may be grouped together in one or more stimulation program groups.

One aspect of programming an IMD is determining the acceptable and efficacious stimulation intensities at which to deliver the electrical stimulation to the patient. Stimulation intensities that are efficacious in treating symptoms of a condition, but do not produce unacceptable side effects generally vary from patient to patient, and, as such, may need to be tested for each patient receiving stimulation from an IMD. As used in this disclosure, stimulation intensity may refer to the amount of energy delivered to a patient through electrical stimulation. As such, stimulation intensity may be a function of both the amplitude, e.g., current or voltage, and the pulse width of the stimulation pulses delivered to the patient during an electrical stimulation session. Changes in stimulation intensity, i.e. increases or decreases, may therefore correspond to a change in one or both of the stimulation amplitude and the pulse width.

One method of testing stimulation intensities for a patient is to establish one or more stimulation thresholds, which may be associated with each of a number of different electrodes or different electrode combinations by which the stimulation is delivered. A stimulation threshold may refer to a level of stimulation intensity at which a patient experiences a perceivable sensation as a result of stimulation delivered at that intensity level. Example stimulation thresholds include perception, parasthesia, discomfort, muscle recruitment, and pain thresholds. Stimulation delivered to a patient may be defined by a range of stimulation intensities within which efficacious therapy is possible without unacceptable side effects. Such a range may be referred to as a usability range and may generally include a lower bound or low stimulation threshold and an upper bound or high stimulation threshold. Example low stimulation thresholds include the perception and parasthesia thresholds. Example high stimulation thresholds include the discomfort, muscle recruitment, and pain thresholds. Defining usability ranges for different individual electrodes or combinations of electrodes by which stimulation will be delivered to the patient may assist in programming by narrowing the range of possible stimulation intensities that may produce efficacious stimulation therapy to the patient. For example, by defining a usability range between a perception and a pain threshold of a patient for a particular electrode or combination of electrodes, testing within that range may result in stimulation intensities that are high enough to produce perceivable effects but not too high so as to produce undesirable side effects, such as pain.

As noted above, a stimulation threshold may refer to a level of stimulation intensity at which a patient experiences a perceivable sensation as a result of stimulation delivered at that intensity level, and different example thresholds include perception, parasthesia, discomfort, muscle recruitment, and pain thresholds. Stimulation thresholds may be determined based on patient feedback, e.g. by increasing the intensity of stimulation until the patient indicates a perceived effect of the stimulation is felt. The perception threshold for an electrode or combination of electrodes may refer to the level of stimulation intensity at which the patient first perceives the electrical stimulation. The paresthesia threshold may refer to the level of stimulation intensity at which the patient first feels a "tingling" sensation as a result of the stimulation. The discomfort threshold may refer to the level of intensity at which the patient feels discomfort an uncomfortable effect of the stimulation. The pain threshold may refer to the level of intensity at which the patient feels pain. Discomfort and pain may both indicate undesirable effects of the stimulation, but the character of the two effects may differ. For example, discomfort may refer to a level of blunt pressure, which, although not painful, is nevertheless uncomfortable for the patient. Discomfort may have a relatively wide range of levels at which the effect becomes increasingly intolerable to the patient. Pain, on the other hand, may refer to a sharp sensation that causes an effect that, as the level of the effect increases, is immediately or quickly becomes intolerable to the patient such that the range of levels at which the pain may be tolerable to the patient may be much narrower than the discomfort range. The muscle recruitment threshold may refer to the level of stimulation intensity at which one or more of the muscles in the area of a nerve of interest begin to twitch. The muscle twitching occurs based on activation of nerves leading to muscles in the area of interest as a result of the stimulation.

In some examples, each electrode on an implanted lead may be associated with at least one threshold. For example, an electrode may deliver stimulation that produces a perception threshold that also corresponds to one or more of a pain, discomfort or muscle recruitment threshold. In another example, an electrode may be associated with a number of thresholds, including, e.g. two or more of any of the perception, paresthesia, pain, discomfort and muscle recruitment thresholds.

Stimulation thresholds may therefore be employed in the context of programming an IMD to deliver efficacious therapy to a patient by facilitating selection of stimulation parameters, e.g. stimulation amplitude and/or pulse width, and individual electrodes or combinations of electrodes that are likely to produce effective results for the patient. Stimulation thresholds may also be employed as a measure of or basis for delivering stimulation therapy in different therapeutic modes, including, e.g. a prophylactic mode configured to inhibit onset of a symptom or multiple symptoms of the chronic condition and an abortive mode configured to reduce an effect or multiple effects of or terminate a symptom of the chronic condition or reduce the duration of the symptomatic period. In this disclosure, a "chronic condition" may refer to a condition that a patient experiences over a long period of time, e.g. longer than six months. A chronic condition, although being characterized by a long duration, may include acute symptoms, the onset of which may be sudden and severe and may not last for a long period of time. Thus, a patient may have a chronic condition for a long period of time that is characterized by periodic acute symptoms, the effects of which last for relatively shorter periods of time. In some cases, a chronic condition may also be characterized by periodic or persistent, less severe symptoms, the onset of which may be gradual.

Some chronic conditions exhibit symptoms that occur periodically, versus persistently or substantially persistently over time. In some cases, the effects of the symptoms are acute in the sense that onset of the symptoms occur rapidly and last for a relatively short period of time, e.g. short in comparison to chronic symptoms the effects of which may be felt persistently over time. Patients with such conditions and exhibiting such acute symptoms may be well served by different modes of electrical stimulation therapy directed at producing different effects depending on whether the patient is currently experiencing an episode of the condition, e.g. currently feeling the effects of one or more symptoms of the condition, or is not currently experiencing an episode. In particular, patients with such conditions including periodic acute symptoms may benefit from a dual mode stimulation regime including periods of prophylactic stimulation therapy during periods when the patient is not experiencing an episode of symptoms and abortive stimulation therapy around the time when an episode is occurring or will occur in the near future.

In some examples, conditions for which dual prophylactic and abortive stimulation modes may be appropriate and advantageous may be more effectively treated by modulating stimulation in the different modes based on patient stimulation thresholds. As described above, stimulation thresholds, and, in particular, ranges of such thresholds, e.g. a usability range between a low stimulation threshold and a high stimulation threshold may assist in programming by narrowing the range of possible stimulation intensities that may produce efficacious stimulation therapy for the patient. For a particular electrode or combination of electrodes through which stimulation is delivered, a patient commonly has a fixed stimulation threshold or set of thresholds for the electrode(s) that does not generally change over time. In the case of conditions with periodic, acute versus chronic symptoms, however, a patient's stimulation threshold may change based on whether or not they are experiencing particular symptoms. In such cases, a number of different sets of stimulation thresholds associated with different symptomatic stages of the patient's condition may be established. For example, a set of one or more stimulation thresholds may be established for the patient, which is associated with patient perception in the absence of any symptoms of the condition. Another set of stimulation thresholds may also be established for the patient, which is associated with patient perception while a symptom of the chronic condition is occurring. In some cases, a third set of stimulation thresholds may be established that are associated with the immediate onset of symptoms of a condition, but before the symptoms are fully in effect. The different sets of stimulation thresholds may then be used as a basis to modulate stimulation delivered to the patient in prophylactic and abortive stimulation modes.

A number of conditions responsive to electrical stimulation therapy may also be well suited for dual prophylactic and abortive stimulation mode therapy. One example condition that may be responsive to dual prophylactic and abortive mode stimulation therapies according to this disclosure is migraine headaches. Most types of migraines are characterized by periodic, acute symptoms for which prophylactic and abortive therapy may generally be beneficial. Additionally, some migraine patients exhibit a particular change in sensitivities from before a migraine occurs to the onset and through the duration of the migraine. In particular, some migraine patients become hypersensitive to external stimuli during a migraine attack. In such cases, the patient's electrical stimulation threshold and their usability range from low to high thresholds may shift generally to lower intensities while the patient is experiencing an effect or multiple effects, e.g. pain from the migraine. Thus, for such patients, prophylactic electrical stimulation may be delivered at a higher intensity level than abortive stimulation, but, in any event, may be modulated based on different sets of stimulation thresholds that are each associated with different symptomatic stages of a migraine. Stimulation of one or more cranial nerves may be effective in treating migraine headaches or other conditions in accordance with examples according to this disclosure. For example, prophylactic and abortive stimulation therapy modes in accordance with this disclosure may be directed to stimulating one or more occipital or trigeminal nerves of a patient. In another example, the disclosed therapies may be directed to stimulating a supraorbital cranial nerve.

Examples according to this disclosure employ techniques for modulating stimulation in prophylactic and abortive therapy modes based multiple sets of one or more stimulation thresholds, each of which sets of threshold(s) are associated with different symptomatic stages of a chronic condition. In one example, prophylactic electrical stimulation is delivered to a cranial nerve based on a first range of stimulation thresholds associated with patient perception in the absence of any symptoms of a chronic condition. The prophylactic stimulation is configured to inhibit onset of a symptom of the chronic condition. Additionally, abortive electrical stimulation is delivered to the cranial nerve based on a second range of stimulation thresholds associated with patient perception while a symptom of the chronic condition is occurring. The abortive stimulation is configured to reduce an effect of a symptom of the chronic condition, which may include terminating the occurrence of the symptom, reducing the extent to which the patient perceives the symptom, or reducing the duration of time over which the symptom occurs.

In another example, prophylactic electrical stimulation configured to inhibit onset of a symptom of a chronic condition is delivered to a cranial nerve of a patient. Abortive electrical stimulation configured to reduce an effect of a symptom of the chronic condition is also delivered to the cranial nerve. In this example, the stimulation intensity of the prophylactic stimulation is greater than the stimulation intensity of the abortive stimulation.

Dual prophylactic and abortive stimulation therapies according to this disclosure are described in detail with reference to FIGS. 6 and 7. However, example electrical stimulation systems including, e.g. implantable stimulators, stimulation leads and electrodes, and external programmers through which such techniques may be applied are first described with reference to FIGS. 1A-5.

FIG. 1A is a conceptual diagram illustrating an example therapy system 10A that includes an implantable medical device (IMD) 12 configured as an electrical stimulator, which is coupled to implantable stimulation leads 14 and 15. In the example of FIG. 1A, IMD 12 is implanted proximate to target stimulation sites 18 and 19 within patient 16. In one example, target stimulation sites 18 and 19 are proximate to an occipital region 11 within patient 16. Occipital region 11 generally encompasses occipital nerve sites of patient 16, which may be, for example, an occipital nerve (e.g., a greater occipital nerve, lesser occipital nerve, and third occipital nerve), tissue adjacent to the occipital nerves, or a nerve branching from the occipital. Thus, reference to an "occipital nerve" throughout the disclosure also includes branches of the occipital, respectively. Similarly reference to a "trigeminal nerve" throughout the disclosure also includes branches of one of the three major divisions of the trigeminal nerve. In addition, the therapy may be delivered to both an occipital nerve and trigeminal nerve by a single therapy system or by separate therapy systems (e.g., by separate electrical stimulators and leads).

IMD 12 provides a programmable stimulation signal (e.g., in the form of electrical pulses or substantially continuous-time signals) that is delivered to target stimulation sites 18 and 19 by implantable medical leads 14 and 15, respectively, and more particularly, via stimulation electrodes carried by leads 14 and 15. IMD 12 may also be referred to as a pulse or signal generator, and in the example shown in FIG. 1, IMD 12 may also be referred to as a neurostimulator. In some examples, lead 14 and/or lead 15 may also carry one or more sense electrodes to permit IMD 12 to sense electrical signals or other physiological parameters (e.g., blood pressure, temperature, etc.) from target stimulation site 18 and/or 19, respectively.

Additionally, IMD 12 may operate in conjunction with other sensors housed by IMD 12 or separate from the device and configured to sense patient parameters, including, e.g. patient posture, activity level, and/or head position. Such conditions may affect the efficacy of stimulation therapy and sensing these conditions may therefore provide feedback signals for closed loop stimulation therapy that automatically changes as a function of one or more of the sensed conditions. For example, IMD 12 may work in conjunction with one or more accelerometers implanted within patient 16 to provide posture responsive stimulation therapy that automatically adjusts based on the posture of the patient sensed by the accelerometers. In another example, IMD 12 may work in conjunction with one or more accelerometers or other sensors configured to sense the position or orientation of the head of patient 16 relative to the patient's torso to provide stimulation therapy that automatically adjusts based on head position. Example techniques for providing adaptive stimulation therapy to a patient based on head position are described in U.S. Patent Application Publication No. 2012/0277833 by Gerber et al., filed Apr. 26, 2012 and entitled "ELECTRICAL STIMULATION THERAPY BASED ON HEAD POSITION," which claims the benefit of U.S. Provisional Application No. 61/481,032, the entire contents of both of which is incorporated herein by reference.

Proximal ends 14A and 15A of leads 14 and 15, respectively, may be both electrically and mechanically coupled to connection ports of connector block 13 of IMD 12 either directly or indirectly (e.g., via a lead extension). In particular, conductors disposed in the lead body of each of leads 14 and 15 may electrically connect stimulation electrodes (and sense electrodes, if present) adjacent to distal ends 14B and 15B of leads 14 and 15, respectively, to IMD 12.

In the example of therapy system 10A shown in FIG. 1A, target stimulation sites 18 and 19 are located within the patient's head (e.g., proximate to one or more occipital nerve) and on opposite sides of midline 9 of patient 16. Midline 9 is a schematic representation of the line that divides patient 16 into approximately equal and symmetrical left and right halves. Delivering therapy to two target tissue sites, such as sites 18 and 19, may be used to deliver therapy to two nerve branches that branch from the same nerve. Nerves may branch into left and right branches that extend to opposite sides of midline 9, and therapy may be delivered to one or both nerve branches on opposite sides of midline 9 (such as at target tissue sites 18 and 19). Stimulation of two nerve branches on opposite sides of midline 9 may be referred to as bilateral stimulation. However, bilateral stimulation may also refer to stimulation of any two regions of patient 16 either sequentially or simultaneously. Delivering therapy at or near nerves branch, e.g., closer to the nerve endings, may allow more targeted therapy delivery with fewer side effects.

Stimulation of the occipital region 11 (i.e., in regions of patient 16 proximate to occipital nerves, a trigeminal nerve or other cranial sites) may help alleviate pain associated with, for example, migraines, cervicogenic headaches, occipital neuralgia or trigeminal neuralgia.

Therapy system 10A, however, is useful in other neurostimulation applications. Thus, in other examples, target stimulation sites 18 and 19 may be at locations proximate to any other suitable nerve in body of patient 16, which may be selected based on, for example, a therapy program selected for a particular patient. For example, in other examples, therapy system 10 may be used to deliver neurostimulation therapy to other areas of the nervous system, in which cases, lead 14 would be implanted proximate to the respective nerve(s). As one example, leads 14 and 15 may be implanted proximate to other nerves and/or structures of the head and neck of patient 16. For example, when therapy system 10 is used for stimulating a trigeminal nerve, target stimulation sites 18 and 19 may be on the side or front of the head of patient 16. In another example, IMD 12 and one or both of leads 14 and 15 may be directed to CNS targeting cranial nerves other than the occipital or trigeminal nerves, including, e.g. a supraorbital nerve. In another example, dual prophylactic and abortive stimulation mode therapies according to this disclosure may be directed to stimulation of one or more peripheral nerves, including, e.g., sacral nerves for the treatment of various conditions including urinary tract dysfunction such as urinary incontinence.

In the illustrated example of FIG. 1A, IMD 12 is implanted in the back of patient 16 over the trapezius muscle (e.g., IMD 12 may be disposed within a surgically formed subcutaneous pocket formed near the trapezius muscle). IMD 12 may be inserted into patient 16 at incision site 17A. Leads 14 and 15 may also be inserted into patient 16 at incision site 17A and advanced (e.g., by tunneling) to target tissue sites 18 and 19, respectively. In this manner, IMD 12, lead 14, and lead 15 may all be inserted using a single incision at incision site 17A. Alternatively, a second incision may be made at incision site 17B to facilitate implantation of leads 14 and 15 within patient 16 and positioning leads 14 and 15 with respect to target tissue sites 18 and 19 to achieve useful stimulation therapy or sensing. In another example, IMD 12 may be implanted at other suitable locations within patient 16, such as but not limited to, in a chest cavity, lower back, lower abdomen, or buttocks of patient 16.

Therapy system 10A also may include a clinician programmer 26 and a patient programmer 28. In another example, system 10A may include one external programmer that functions as both a physician and patient programmer, e.g. based on user credentials input by the user to access functions on the programmer. Clinician programmer 26 may be a handheld computing device that permits a clinician to program neurostimulation therapy for patient 16, e.g., using input keys and a display. For example, using clinician programmer 26, the clinician may initiate a protocol to determine stimulation thresholds for each electrode on leads 14 and 15. Based on the determined stimulation thresholds, the clinician may map the location of electrodes on leads 14 and 15 and specify stimulation parameters for use in delivery of electrical stimulation therapy. Clinician programmer 26 supports telemetry (e.g., radio frequency telemetry) with IMD 12 to download neurostimulation parameters and, optionally, upload operational or physiological data stored by IMD 12. In this manner, the clinician may periodically interrogate IMD 12 to evaluate efficacy and, if necessary, modify the stimulation parameters.

Like clinician programmer 26, patient programmer 28 may be a handheld computing device. Patient programmer 28 may also include a display and input keys to allow patient 16 to interact with patient programmer 28 and IMD 12. In this manner, patient programmer 28 provides patient 16 with an interface for control of neurostimulation therapy by IMD 12. For example, patient 16 may use patient programmer 28 to start, stop or adjust neurostimulation therapy. In particular, patient programmer 28 may permit patient 16 to adjust stimulation parameters such as duration, amplitude, pulse width and pulse rate, within an adjustment range specified by the clinician via clinician programmer 28, or select from a library of stored stimulation therapy programs. Patient programmer 28 may, in some examples, be employed to initiate and control the duration of abortive stimulation therapy delivered by IMD 12 to patient 16.

IMD 12, clinician programmer 26, and patient programmer 28 may communicate via cables or a wireless communication, as shown in FIG. 1A. Clinician programmer 26 and patient programmer 28 may, for example, communicate via wireless communication with IMD 12 using known RF telemetry techniques, including, e.g. RF communication according to the 802.11 or Bluetooth specification sets, or other wireless communication techniques, including infrared communication, e.g., according to the IrDA standard, or other standard or proprietary telemetry protocols.

However, clinician programmer 26 and patient programmer 28 need not communicate wirelessly. For example, in other examples, programmers 26 and 28 may communicate via a wired connection, such as via a serial communication cable, or via exchange of removable media, such as magnetic or optical disks, or memory cards or sticks. Further, the clinician programmer 26 may communicate with patient programmer 28 via remote telemetry techniques, or via a local area network (LAN), wide area network (WAN), public switched telephone network (PSTN), or cellular telephone network, for example.

Stimulation thresholds for one or more electrodes on one or both of leads 14 and 15 may be employed in the context of programming IMD 12, e.g. via clinician programmer 26 and/or patient programmer 28 to deliver efficacious therapy to patient 16 by facilitating selection of stimulation parameters, e.g. stimulation amplitude and/or pulse width, and individual electrodes or combinations of electrodes that are likely to produce effective results for the patient. Additionally, stimulation thresholds may be employed to physically map the position of different electrodes on leads 14 and 15 within the body of patient 16 relative to target stimulation sites 18 and 19, e.g. relative to one or more occipital nerves, thereby potentially reducing the costs, complexity, and risks of procedures used to implant IMD 12 and leads 14 and 15.

In one example, clinician programmer 26, or another external programmer communicatively connected to IMD 12, e.g. patient programmer 28 is employed to identify a stimulation threshold for each electrode connected to leads 14 and 15 arranged adjacent target stimulation sites 18 and 19, e.g. adjacent one or more occipital nerves of patient 16. Programmer 26 and/or IMD 12 may be configured to map the location of the target occipital nerve(s) relative to the electrodes of leads 14 and 15 based on the stimulation threshold of each of the electrodes. A clinician may employ programmer 26 to select an individual electrode or combination of electrodes on one or both of leads 14 and 15 through which IMD 12 may provide stimulation to the occipital nerve(s) at or near target stimulation sites 18 and 19 based, at least in part, on the location of the nerve relative to the selected electrode or electrode combination. In one example, the clinician also employs programmer 26 to create a stimulation program according to which IMD 12 may provide stimulation to the occipital nerve via the selected electrode or electrode combination. The stimulation program may include various values for different stimulation parameters, including, e.g. stimulation amplitude, pulse width, and frequency. In one example, the program is created and stored on programmer 26, in which case programmer 26 may transmit the stimulation program to patient programmer 28 and/or IMD 12. IMD 12 may deliver stimulation to occipital nerve(s) of patient 16 via electrodes on lead 14 and/or 15 according to the stimulation program in order to test the efficacy of the program or to provide chronic therapy to the patient to treat symptoms of one or more conditions, e.g. occipital neuralgia or migraines.

IMD 12, alone or in conjunction with one or both of programmers 26 and 28, may be configured to modulate stimulation delivered to patient 16 in prophylactic and abortive therapy modes based multiple sets of one or more stimulation thresholds, each of which sets of threshold(s) are associated with different symptomatic stages of a chronic condition of the patient. In one example, IMD 12 is configured to deliver prophylactic electrical stimulation to target stimulation sites 18 and 19 via electrodes on leads 14 and 15 based on a first range of stimulation thresholds associated with perception of patient 16 in the absence of any symptoms of a chronic condition. The prophylactic stimulation delivered by IMD 12 is configured to inhibit onset of a symptom of a chronic condition. In one example, IMD 12 delivers prophylactic stimulation to one or more of occipital or trigeminal nerves of patient 16 to inhibit onset of symptoms of a chronic condition, such as pain associated with migraine headaches or occipital or trigeminal neuralgia. Additionally, IMD 12 is configured to deliver abortive electrical stimulation to target stimulation sites 18 and 19 via electrodes on leads 14 and 15 based on a second range of stimulation thresholds associated with perception of patient 16 while a symptom of the chronic condition is occurring. The abortive stimulation delivered by IMD 12 is configured to reduce an effect of a symptom of the chronic condition. In one example, IMD 12 delivers abortive stimulation to one or more of occipital or trigeminal nerves of patient 16 to treat effects of a chronic condition, such as pain associated with migraine headaches or occipital or trigeminal neuralgia.

In another example, IMD 12 is configured to deliver prophylactic electrical stimulation to target stimulation sites 18 and 19 via electrodes on leads 14 and 15 in order to inhibit onset of a symptom of a chronic condition. IMD 12 may also be configured to deliver abortive electrical stimulation to target stimulation sites 18 and 19 via electrodes on leads 14 and 15 in order to reduce an effect of a symptom of the chronic condition. In this example, IMD 12 delivers the prophylactic stimulation at a stimulation intensity that is greater than the stimulation intensity at which the device delivers the abortive stimulation.

Figure 1B:
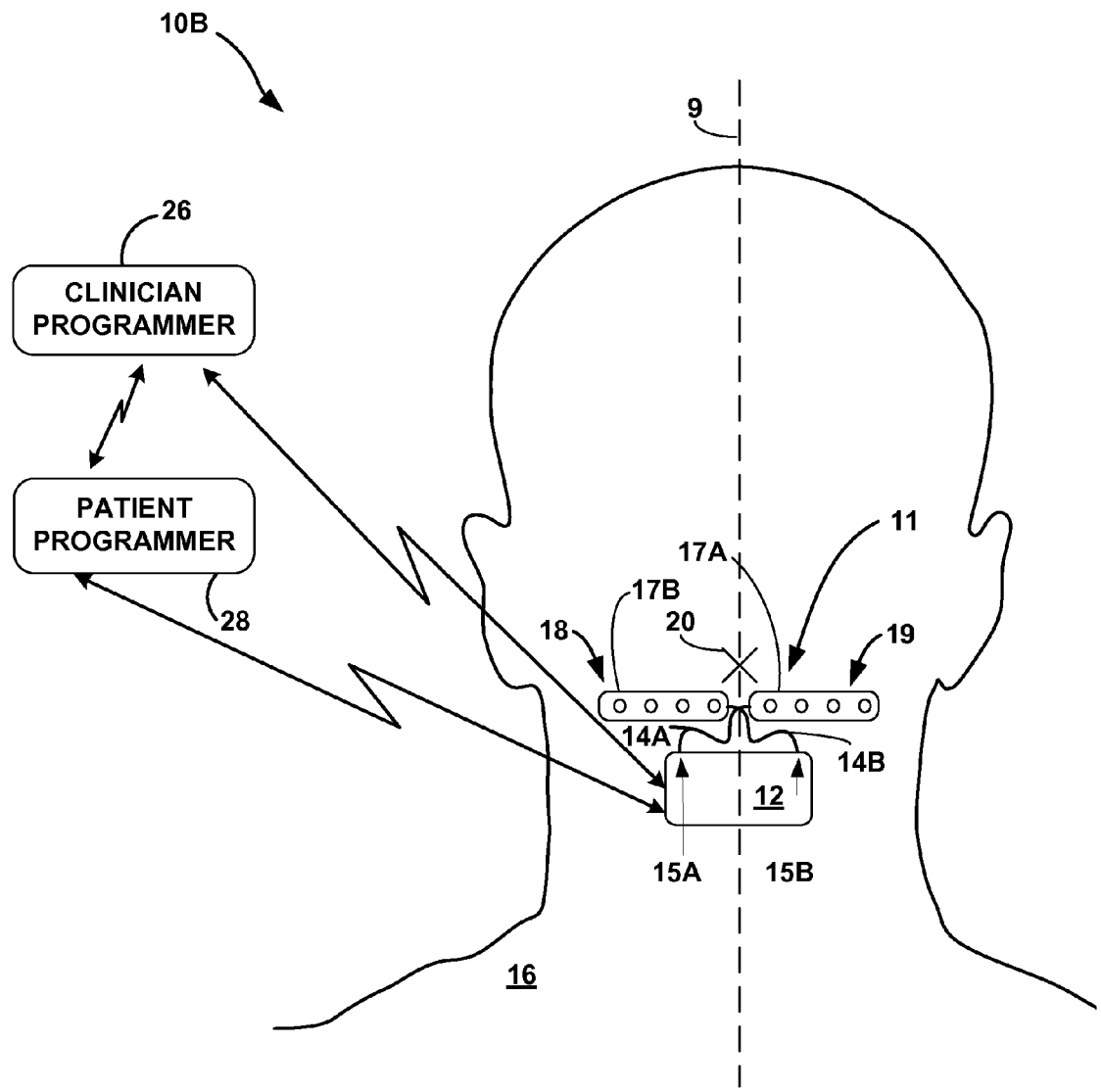
FIG. 1B is a conceptual diagram illustrating another example therapy system that includes an implantable stimulator coupled to an implantable stimulation lead.

FIG. 1B is a conceptual diagram illustrating an example therapy system 10B that includes an implantable IMD 12 coupled to implantable stimulation leads 21A and 21B connected to paddles 22A and 22B (collectively referred to as "paddles 22"), respectively. In the example of FIG. 1B, IMD 12 is implanted in a human patient 16 proximate to an occipital region 11 within patient 16, below inion 20, the craniometric point that is the most prominent point at the occipital protuberance on the back of the head of patient 16. Similar to leads 14 and 15 of FIG. 1A, paddles 17 include electrode sets to deliver stimulation therapy to a therapy region, which generally encompasses occipital nerve sites and trigeminal nerve sites of patient 16. Various techniques as discussed above with respect to FIG. 1A may be employed using therapy system 10B. For example, IMD 12 may be configured to modulate stimulation delivered to patient 16 via implantable stimulation leads 21A and 21B connected to paddles 22A and 22B in prophylactic and abortive therapy modes based multiple sets of one or more stimulation thresholds, each of which set of threshold(s) is associated with different symptomatic stages of a chronic condition of the patient. In some instances, minor modifications may be made, for example, in instances where paddles 17 may include more than one row of electrodes.

Figure 2:
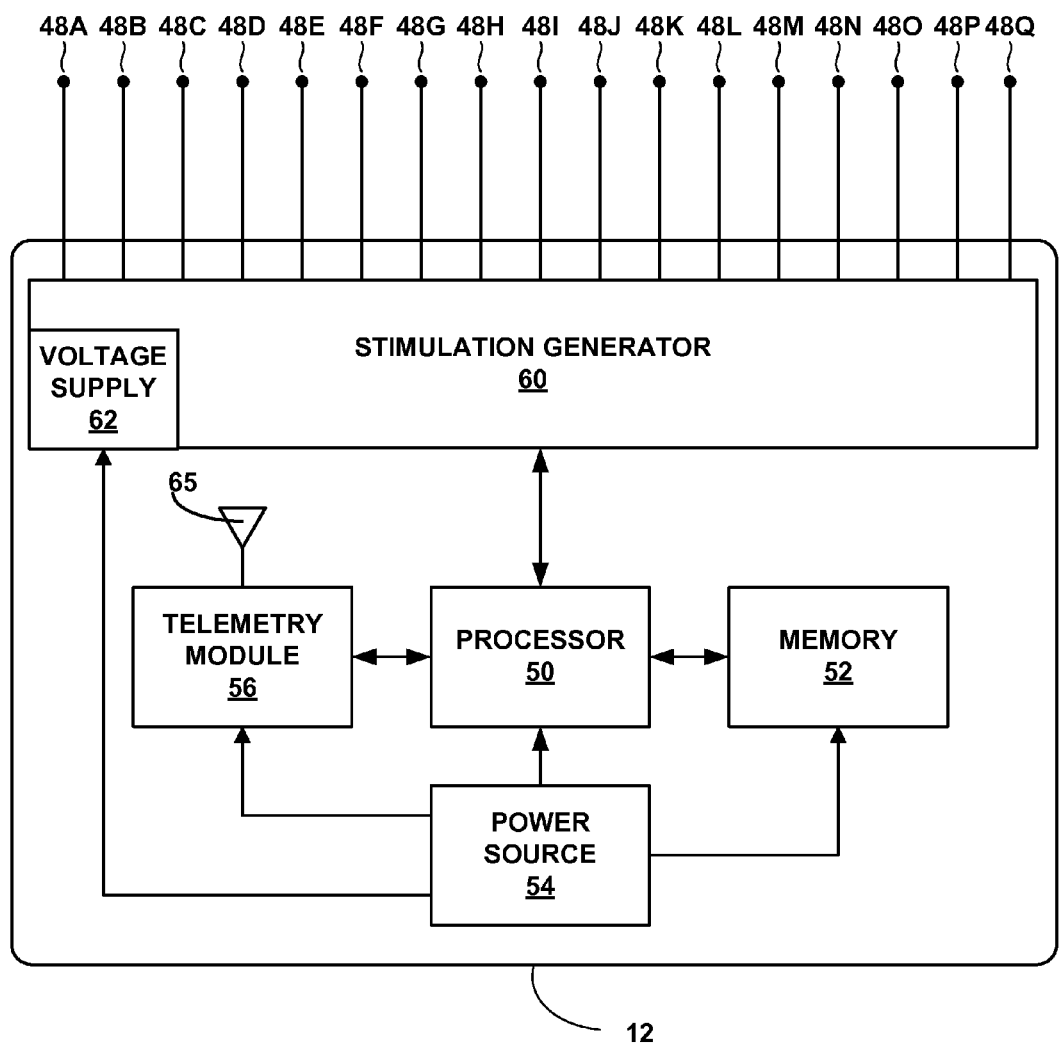
FIG. 2 is a block diagram illustrating various example components of an implantable electrical stimulator.

FIG. 2 is a block diagram illustrating various components of an example configuration of IMD 12 in system 10. In some cases, the components of FIG. 2 may be implemented in an external stimulator. In the example of FIG. 2, IMD 12 includes processor 50, memory 52, power source 54, telemetry module 56, antenna 65, and a stimulation generator 60. IMD 12 is also shown in FIG. 2 coupled to electrodes 48A-Q (collectively "electrodes 48").

Processor 50 may include one or more microprocessors, digital signal processors (DSPs), application-specific integrated circuits (ASICs), field-programmable gate arrays (FPGAs), or other digital logic circuitry. Processor 50 controls operation of IMD 12, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with pulse current amplitudes (i.e., levels), pulse widths (if applicable), and pulse rates specified by one or more stimulation programs.

Memory 52 may store instructions for execution by processor 50, stimulation therapy data, sensor data, and/or other information regarding therapy for patient 16. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and IMD 12 in this disclosure. For example, memory 52 may store one or more prophylactic stimulation mode programs and one or more abortive stimulation mode programs executable by processor 50 to control stimulation generator 60 to deliver stimulation to patient 16 via one or more of electrodes 48A-Q.

Stimulation generator 60 forms a therapy delivery module of IMD 12. Processor 50 controls stimulation generator 60 to deliver electrical stimulation via electrode combinations formed by electrodes 48A-Q. For example, stimulation generator 60 may deliver electrical stimulation therapy via electrodes on one or more of leads 14 and 15, e.g., as stimulation pulses or continuous waveforms. Stimulation generator 60 may include stimulation generation circuitry to generate stimulation pulses or waveforms and switching circuitry to switch the stimulation across different electrode combinations, e.g., in response to control by processor 50. In particular, processor 50 may control the switching circuitry on a selective basis to cause stimulation generator 60 to deliver electrical stimulation to selected electrode combinations and to shift the electrical stimulation to different electrode combinations when the therapy is delivered to a different locations within patient 16. In other examples, stimulation generator 60 may include multiple current sources to drive more than one electrode combination at one time. In this case, stimulation generator 60 may decrease current to the first electrode combination and simultaneously increase current to the second electrode combination to shift the stimulation therapy.

An electrode configuration, e.g., electrode combination and associated electrode polarities, may be represented by data stored in a memory location, e.g., in memory 52, of IMD 12. Processor 50 may access the memory location to determine the electrode combination and control stimulation generator 60 to deliver electrical stimulation via the indicated electrode combination. To adjust electrode combinations, amplitudes, pulse rates, or pulse widths, processor 50 may command stimulation generator 60 to make the appropriate changes to therapy according to instructions within memory 52 and rewrite the memory location to indicate the changed therapy. In other examples, rather than rewriting a single memory location, processor 50 may make use of two or more memory locations.

When activating stimulation, processor 50 not only accesses the memory location specifying the electrode combination but also other memory locations specifying various stimulation parameters such as voltage or current amplitude, pulse width and pulse rate. Stimulation generator 60, e.g., under control of processor 50, then makes use of the electrode combination and parameters in formulating and delivering the electrical stimulation to patient 12.

According to examples described herein, such stimulation parameters may be adjusted to modify stimulation therapy delivered by IMD 12 based on the symptomatic stage of a chronic condition of patient 16. For example, stimulation parameters may be adjusted to modify stimulation therapy delivered by IMD 12 such that the IMD delivers therapy according to a combination of prophylactic and abortive stimulation modes depending on the symptoms, if any, experienced by patient 16.

In one example, processor 50 of IMD 12 is configured to control stimulation generator 60 to deliver prophylactic electrical stimulation to target stimulation sites 18 and 19 via one or more of electrodes 48A-Q on leads 14 and/or 15 based on a first range of stimulation thresholds associated with perception of patient 16 in the absence of any symptoms of a chronic condition. The prophylactic stimulation delivered by stimulation generator 60 under the control of processor 50 of IMD 12 is configured to inhibit onset of a symptom of a chronic condition. In one example, processor 50 controls stimulation generator 60 to deliver prophylactic stimulation to one or more of occipital or trigeminal nerves of patient 16 to inhibit onset of symptoms of a chronic condition, such as pain associated with migraine headaches or occipital or trigeminal neuralgia. Additionally, processor 50 of IMD 12 is configured to control stimulation generator 60 to deliver abortive electrical stimulation to target stimulation sites 18 and 19 via one or more of electrodes 48A-Q on leads 14 and/or 15 based on a second range of stimulation thresholds associated with perception of patient 16 while a symptom of the chronic condition is occurring. The abortive stimulation delivered by stimulation generator 60 is configured to reduce an effect of a symptom of the chronic condition. In one example, processor 50 controls stimulation generator 60 deliver abortive stimulation to one or more of occipital or trigeminal nerves of patient 16 to treat effects of a chronic condition, such as pain associated with migraine headaches or occipital or trigeminal neuralgia.

In another example, processor 50 of IMD 12 is configured to control stimulation generator 60 to deliver prophylactic electrical stimulation to target stimulation sites 18 and 19 via one or more electrodes 48A-Q on leads 14 and/15 in order to inhibit onset of a symptom of a chronic condition. Processor 50 of IMD 12 may also be configured to control stimulation generator 60 to deliver abortive electrical stimulation to target stimulation sites 18 and 19 via combinations of electrodes 48A-Q on leads 14 and/or 15 in order to reduce an effect of a symptom of the chronic condition. In this example, processor 50 may control stimulation generator 60 to deliver the prophylactic stimulation at a stimulation intensity that is greater than the stimulation intensity at which IMD 12 delivers the abortive stimulation, e.g. according to stimulation parameters including intensity stored in one or more programs on memory 52 as described in more detail below.

An exemplary range of electrical stimulation parameters likely to be effective in treating the effects of symptoms of a chronic condition related to one or more cranial nerves of patient 16, e.g. pain associated with migraine headaches or occipital or trigeminal neuralgia, are listed below. While stimulation pulses are described, stimulation signals may be of any of a variety of forms such as sine waves or the like.

1. Pulse Rate: between approximately 4 Hz and approximately 1200 Hz, more preferably between approximately 4 Hz and approximately 130 Hz, and still more preferably between approximately 40 Hz and approximately 60 Hz.

2. Amplitude: between approximately 0.1 volts and approximately 10.5 volts. In other examples, the amplitude may be specified or measured in terms of a current amplitude a current amplitude that is delivered to the patient. For example, the range of current amplitude may be between approximately 0.1 milliamps (mA) and approximately 20 mA.

3. Pulse Width: between approximately 10 microseconds and approximately 1000 microseconds, more preferably between approximately 100 microseconds and approximately 200 microseconds.

Depending on the application, different ranges of parameter values may be used by IMD 12, and, in particular, processor 50 to control stimulation generator 60 to deliver stimulation via one or more of electrodes 48A-Q on leads 14 and/15 to patient 16.

Processor 50 accesses stimulation parameter values stored by memory 52, e.g., as therapy programs and groups of programs. Upon selection of a particular program group, processor 50 controls stimulation generator 60 to deliver stimulation according to the programs in the groups, e.g., simultaneously or on a time-interleaved basis. A therapy group may include a single program or multiple programs. In one example, one program group may include multiple prophylactic stimulation programs and another program group stored on memory 52 and executable by processor 50 may include multiple abortive stimulation programs. As mentioned previously, each therapy program specifies values for a set of stimulation parameters, such as amplitude, pulse width, and pulse rate. In addition, each program may specify a particular electrode combination for delivery of stimulation. Again, the electrode combination may specify particular electrodes in a single array or multiple arrays, e.g., particular combinations of electrodes 48A-Q on leads 14 and/or 15.

Electrodes 48A-48P are implantable and may be deployed on one or more implantable leads. With respect to FIG. 1A, leads 14 and 15 may carry electrodes 48A-H and electrodes 48I-P, respectively. In some cases, one or more additional electrodes, such as electrode 48Q, may be located on or within the housing of IMD 12, e.g., to provide a common or ground electrode or a housing anode or cathode. In the example of FIG. 1A, each of leads 14 and 15 carries eight electrodes to provide an 2×8 electrode configuration (two leads with 8 electrodes each), providing a total of sixteen different electrodes. The leads may be detachable from a housing associated with IMD 12, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), two leads with four electrodes each (2×4), three leads with four electrodes each (3×4), three leads with eight electrodes each (3×8), three leads with four, eight, and four electrodes, respectively (4-8-4), or other configurations. Different electrodes are selected and assigned different polarities to form electrode combinations.

Electrode 48Q represents one or more electrodes that may be carried on a housing, i.e., can, of IMD 12. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of IMD 12, such as stimulation generator 60, processor 50, memory 52, telemetry module 56, and power source 54.

Wireless telemetry in IMD 12, e.g. with an external programmer, e.g., clinician programmer 26 or patient programmer 28, or another device may be accomplished by radio frequency (RF) communication or proximal inductive interaction of IMD 12 with the external programmer. Telemetry module 56 may send information to and receive information from the external programmer via antenna 65 on a continuous basis, at periodic intervals, at non-periodic intervals, or upon request from the stimulator or programmer. To support RF communication, telemetry module 56 may include appropriate electronic components, such as amplifiers, filters, mixers, encoders, decoders, and the like.

Power source 54 delivers operating power to the components of IMD 12. Power source 54 may include a small rechargeable or non-rechargeable battery and a power generation circuit to produce the operating power. Recharging may be accomplished through proximal inductive interaction between an external charger and an inductive charging coil within IMD 12. In some embodiments, power requirements may be small enough to allow IMD 12 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 12 when needed or desired.

Figure 3:
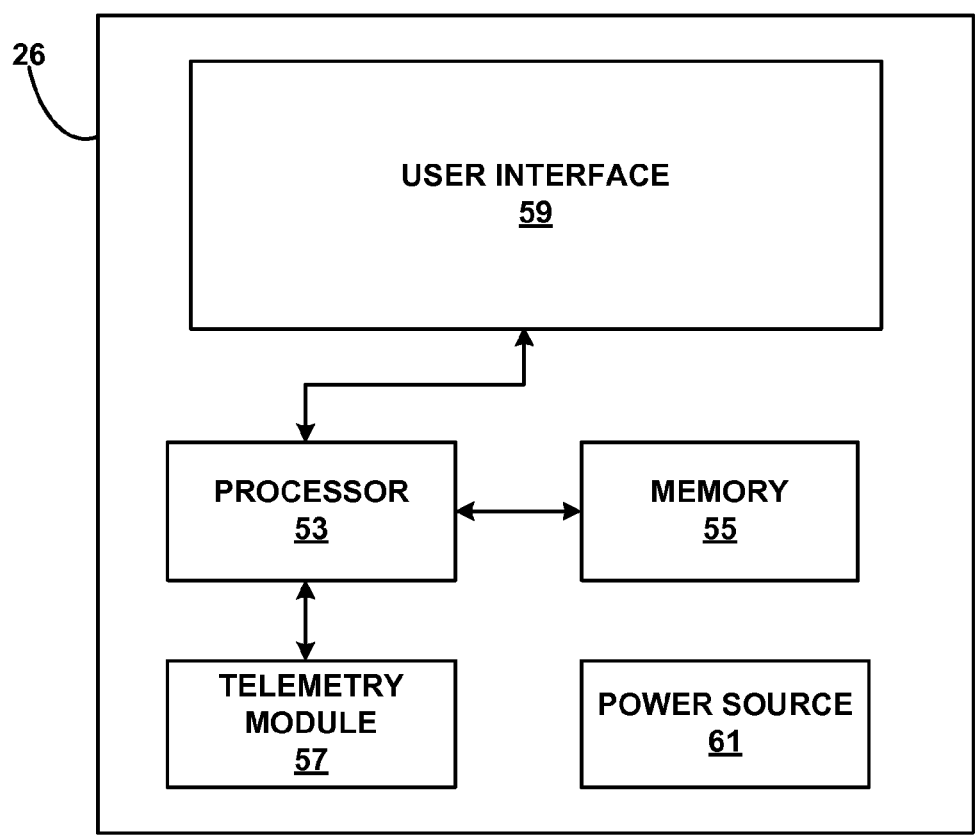
FIG. 3 is a block diagram illustrating various example components of an external programmer for use with an electrical stimulator.

FIG. 3 is a functional block diagram illustrating example components of external programmer 26 for an implantable stimulator such as stimulator 12 (FIG. 1). Although the components shown in FIG. 3 are described in reference to clinician programmer 26, some or all of the components may also be included within patient programmer 28 as shown in FIG. 1. As shown in FIG. 3, clinician programmer 26 includes processor 53, memory 55, telemetry module 57, user interface 59, and power source 61. In general, processor 53 controls user interface 59, stores and retrieves data to and from memory 55, and controls transmission of data with IMD 12 through telemetry module 57. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 26 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 26 is used to program therapy for another patient. Memory 55 may also store information that controls operation of IMD 12, such as therapy delivery values.

A clinician or patient 16 interacts with user interface 59 in order to, for example, manually select, change or modify programs, adjust voltage or current amplitude, provide efficacy feedback, or view stimulation data. In some examples, the user interface 59 is used to perform an initial programming protocol. User interface 59 may include a screen and one or more input buttons that allow external programmer 26 to receive input from a user. In some examples, a clinician interacts with user interface 59 to choose electrodes for stimulation therapy based on a display of the location of the nerve to be stimulated relative to the implanted electrodes 48A-48P. The screen may be a liquid crystal display (LCD), plasma display, dot matrix display, or touch screen. The input buttons may include a touch pad, increase and decrease buttons, emergency shut off button, and other input media needed to control the stimulation therapy.

Telemetry module 57 allows the transfer of data to and from stimulator 12. Telemetry module 57 may communicate automatically with stimulator 12 at a scheduled time or when the telemetry module detects the proximity of the stimulator. Alternatively, telemetry module 57 may communicate with stimulator 12 when signaled by a user through user interface 59. To support RF communication, telemetry module 57 may include appropriate electronic components, such as amplifiers, filters, mixers, encoders, decoders, and the like.

Programmer 26 may communicate wirelessly with IMD 12 using, for example, RF communication or proximal inductive interaction. This wireless communication is possible through the use of telemetry module 57 which may be coupled to an internal antenna or an external antenna. Telemetry module 57 may be similar to telemetry module 56 of IMD 12.

Programmer 26 may also be configured to communicate with another computing device via wireless communication techniques, or direct communication through a wired, e.g., network, connection. Examples of local wireless communication techniques that may be employed to facilitate communication between programmer 26 and another computing device include RF communication based on the 802.11 or Bluetooth specification sets, infrared communication, e.g., based on the IrDA standard.

Power source 61 delivers operating power to the components of programmer 26. Power source 61 may be a rechargeable battery, such as a lithium ion or nickel metal hydride battery. Other rechargeable or conventional batteries may also be used. In some cases, external programmer 26 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

In some examples according to this disclosure, processor 53 of programmer 26 (or a processor of another external device, e.g. patient programmer 28), instead of processor 50 of IMD 12, may be employed to control stimulation generator 60 to deliver stimulation to patient 16 via combinations of electrodes 48A-Q on leads 14 and/or 15. In one example, processor 53 may control stimulation generator 60 by communicating with IMD 12 via telemetry modules 56 and 57 to deliver therapy according to a combination of prophylactic and abortive stimulation modes depending on the symptoms, if any, experienced by patient 16.

In one example, processor 53 of clinician programmer 26 is configured to control stimulation generator 60 to deliver prophylactic electrical stimulation to target stimulation sites 18 and 19 via one or more of electrodes 48A-Q on leads 14 and/or 15 based on a first range of stimulation thresholds associated with perception of patient 16 in the absence of any symptoms of a chronic condition. The prophylactic stimulation delivered by stimulation generator 60 under the control of processor 53 of clinician programmer 26 is configured to inhibit onset of a symptom of a chronic condition. In one example, processor 53 controls stimulation generator 60 to deliver prophylactic stimulation to one or more of occipital or trigeminal nerves of patient 16 to inhibit onset of symptoms of a chronic condition, such as pain associated with migraine headaches or occipital or trigeminal neuralgia. Additionally, processor 53 of clinician programmer 26 is configured to control stimulation generator 60 to deliver abortive electrical stimulation to target stimulation sites 18 and 19 via one or more of electrodes 48A-Q on leads 14 and/or 15 based on a second range of stimulation thresholds associated with perception of patient 16 while a symptom of the chronic condition is occurring. The abortive stimulation delivered by stimulation generator 60 is configured to reduce an effect of a symptom of the chronic condition. In one example, processor 53 controls stimulation generator 60 deliver abortive stimulation to one or more of occipital or trigeminal nerves of patient 16 to treat effects of a chronic condition, such as pain associated with migraine headaches or occipital or trigeminal neuralgia.

In another example, processor 53 of clinician programmer 26 is configured to control stimulation generator 60 to deliver prophylactic electrical stimulation to target stimulation sites 18 and 19 via one or more electrodes 48A-Q on leads 14 and/15 in order to inhibit onset of a symptom of a chronic condition. Processor 53 may also be configured to control stimulation generator 60 to deliver abortive electrical stimulation to target stimulation sites 18 and 19 via combinations of electrodes 48A-Q on leads 14 and/or 15 in order to reduce an effect of a symptom of the chronic condition. In this example, processor 53 may control stimulation generator 60 to deliver the prophylactic stimulation at a stimulation intensity that is greater than the stimulation intensity at which IMD 12 delivers the abortive stimulation, e.g. according to stimulation parameters including intensity stored in one or more programs on memory 55 as described in more detail below.

In some examples, components of IMD 12 may work in conjunction with components of one or both of clinician programmer 26 and patient programmer 28 to deliver stimulation therapy to patient 16 in accordance with this disclosure. For example, processor 50 of IMD 12 may control stimulation generator 60 during prophylactic stimulation modes, while processor 53 of clinician programmer 26 controls stimulation generator 60 during abortive stimulation modes, or vice versa. Other examples of IMD 12 and one or both of clinician programmer 26 and patient programmer 28 functioning together to deliver stimulation therapy to patient 16 in accordance with this disclosure are also contemplated.

Figure 4A:
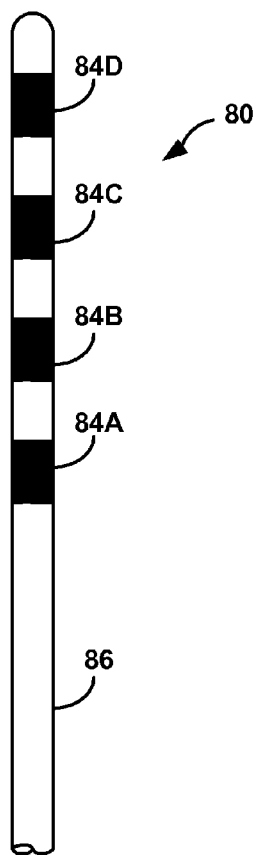
FIGS. 4A and 4B are conceptual diagrams illustrating example leads and electrode configurations that may be used for delivering electrical stimulation therapy as described in this disclosure.
Figure 4B:
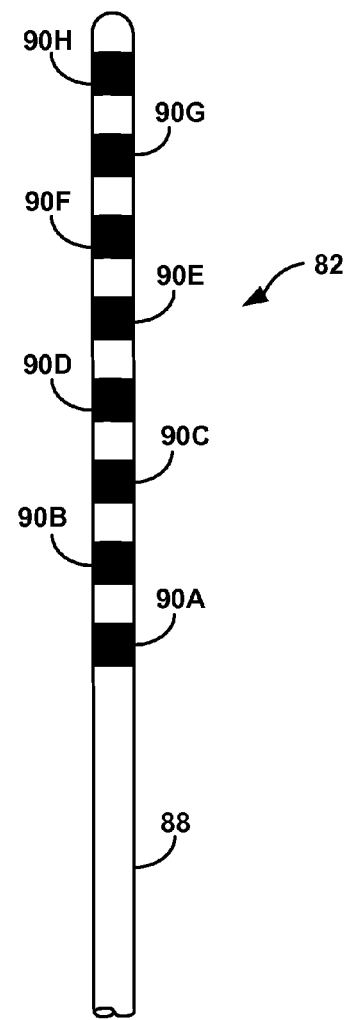

FIGS. 4A and 4B are conceptual diagrams illustrating two different implantable stimulation leads. Leads 80 and 82 are examples of leads 14 and 15 shown in FIG. 1A. As shown in FIG. 4A, lead 80 includes four electrodes 84A-84D mounted at various lengths of lead body 86. Lead 82 includes lead body 88, carrying eight electrodes 90A-90H. Electrodes 84A-84D may be equally spaced along the axial length of lead body 86 at different axial positions. Although not depicted, in some examples, each electrode 84, 90 may formed by two or more electrode segments located at different angular positions around the circumference of lead body 86 or 88, forming segmented electrodes.

Electrodes of one circumferential location may be lined up on an axis parallel to the longitudinal axis of lead 80 or 82. Alternatively, different electrodes may be staggered around the circumference of lead body 86. In addition, lead 80 or 82 may include asymmetrical electrode locations around the circumference of each lead or electrodes of the same level that have different sizes. These electrodes may include semi-circular electrodes that may or may not be circumferentially aligned. Lead body 86 or 88 may include a radio-opaque stripe (not shown) along the outside of the lead body. Each electrode may be substantially rectangular in shape. Alternatively, the individual electrodes may have alternative shapes, e.g., circular, oval, triangular, or the like.

Figure 5:
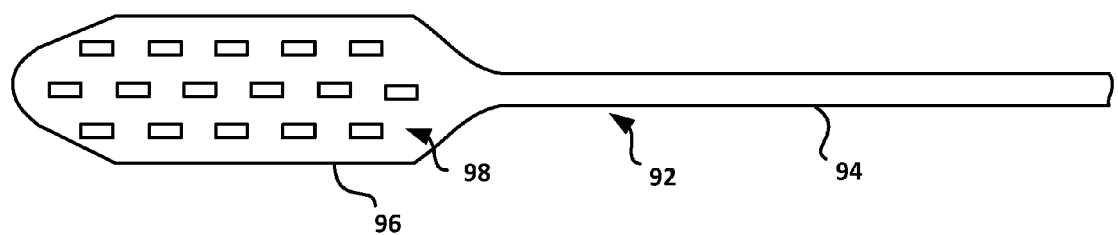
FIG. 5 is a conceptual diagram illustrating an example paddle lead that may be used for delivering electrical stimulation therapy as described in this disclosure.

FIG. 5 is a conceptual diagram illustrating an example paddle lead 92 that additionally or alternatively may be used for delivering electrical stimulation in accordance with the techniques in this disclosure. In the example of FIG. 5, lead 92 includes a lead body 94 and a lead paddle section 96 carrying an array of electrodes 98 arranged in three rows having five, six and five electrodes, respectively. Paddle lead 92 may be configured to include lesser or greater numbers of electrodes. In some implementations, paddle lead 92 may be similar to the Specify™ 5-6-5 paddle lead commercially available from Medtronic, Inc. of Minneapolis, Minn.

Figure 6:
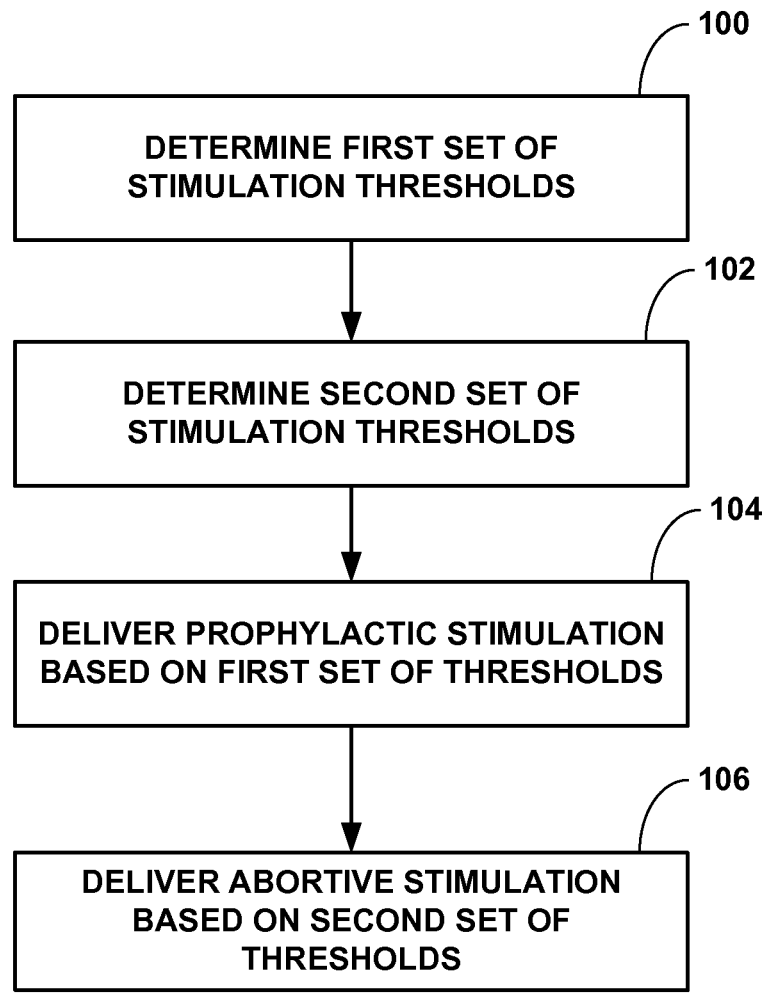
FIG. 6 is a flow diagram illustrating an example method of delivering therapy to a patient including prophylactic and abortive electrical stimulation modes.

FIG. 6 is a flow diagram illustrating an example method of delivering therapy to a patient including prophylactic and abortive electrical stimulation modes. The example method of FIG. 6 includes determining a first set of stimulation thresholds associated with patient perception in the absence of any symptoms of a chronic condition (100), determining a second set of stimulation thresholds associated with patient perception while a symptom of the chronic condition is occurring (102), delivering prophylactic electrical stimulation to a cranial nerve based on a first range of stimulation thresholds associated with patient perception in the absence of any symptoms of a chronic condition (104), delivering abortive electrical stimulation to the cranial nerve based on a second range of stimulation thresholds associated with patient perception while a symptom of the chronic condition is occurring (106). The prophylactic stimulation is configured to inhibit onset of a symptom of the chronic condition. The abortive stimulation is configured to reduce an effect of a symptom of the chronic condition.

The functions of the method of FIG. 6 for delivering therapy to a patient including prophylactic and abortive electrical stimulation modes are described as executed by IMD 12, and in particular, processor 50, memory 52, and stimulation generator 60 of IMD 12. However, in other examples, one or more of these functions may be carried out by other devices including, e.g., one or both of clinician programmer 26 and patient programmer 28. For example, dual prophylactic and abortive stimulation mode therapies may be delivered by stimulation generator 60 under the control of processor 53 if clinician programmer 26 based on stimulation parameters and other information stored in memory 55. Alternatively, one or more of the functions associated with the method of FIG. 6 may be executed by processor 53 of programmer 26, while the remaining functions are executed by processor 50 of IMD 12. Other combinations of distributing the execution functions of the method of FIG. 6 among a number of devices to deliver prophylactic and abortive electrical stimulation to a patient are possible, including employing external devices communicatively connected to IMD 12 other than programmer 26, e.g. employing patient programmer 28 to execute one or more of the functions of the method of FIG. 6.

The example method of FIG. 6 includes determining a first set of stimulation thresholds associated with patient perception in the absence of any symptoms of a chronic condition (100) and determining a second set of stimulation thresholds associated with patient perception while a symptom of the chronic condition is occurring (102). A stimulation threshold may refer to a level of stimulation intensity at which a patient experiences a perceivable sensation as a result of stimulation delivered at that intensity level. Example stimulation thresholds include perception, parasthesia, discomfort, muscle recruitment, and pain thresholds. Stimulation delivered to a patient may be defined by a range of stimulation intensities within which efficacious therapy is possible without unacceptable side effects. Such a range may be referred to as a usability range and may generally include a lower bound or low stimulation threshold and an upper bound or high stimulation threshold. Example low stimulation thresholds include the perception and parasthesia thresholds. Example high stimulation thresholds include the discomfort, muscle recruitment, and pain thresholds.

Figure 7:
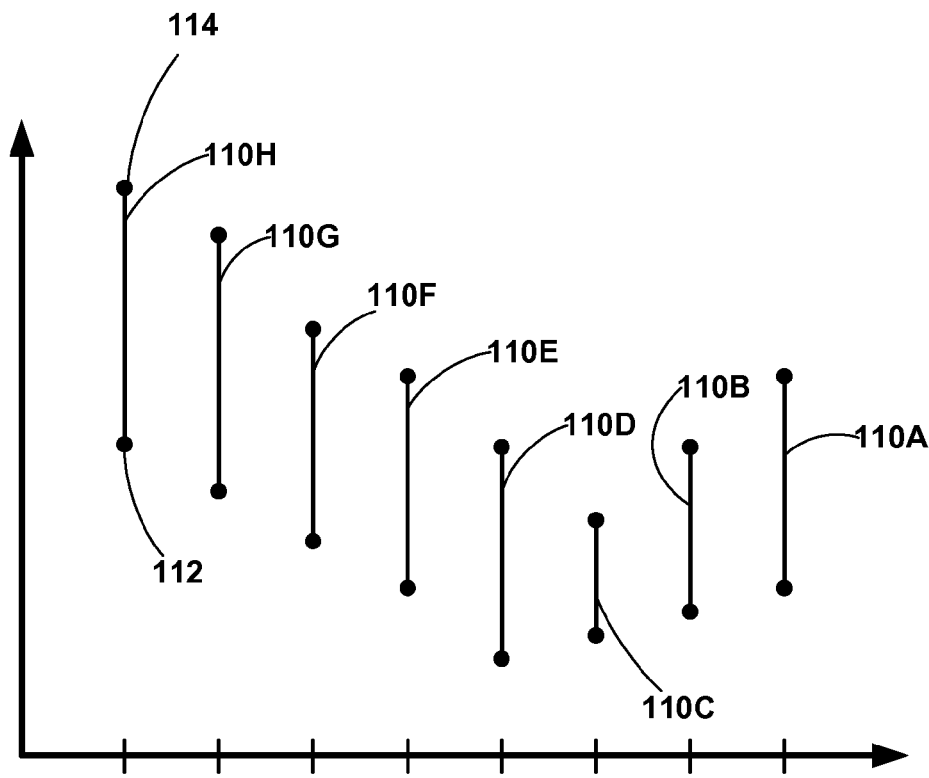
FIG. 7 is a graph illustrating a number of ranges of stimulation thresholds associated with a number of electrodes on a lead.
Figure 7:
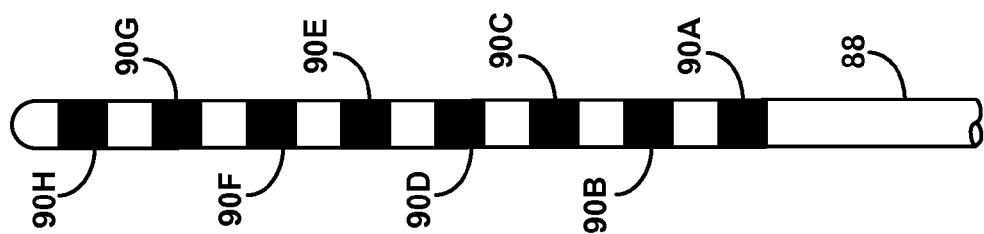

FIG. 7 is a graph illustrating a number of ranges of stimulation thresholds associated with a number of electrodes on a lead. In FIG. 7, usability ranges 110A-110H are illustrated for electrodes 90A-90H on example eight electrode lead 88 of FIG. 4B. Usability ranges 110A-110H are ranges of stimulation intensities bounded by two stimulation thresholds for each of the respective electrodes 90A-90H. For example, usability range 110H for electrode 90H illustrates that each of the usability ranges may include a low stimulation threshold, e.g. low threshold 112 for usability range 110H, and a high stimulation threshold, e.g. high threshold 114 for threshold range 110H. As noted above, example low stimulation thresholds include the perception and parasthesia thresholds and example high stimulation thresholds include the discomfort, muscle recruitment, and pain thresholds.

Referring again to the example method of FIG. 6, determining different stimulation thresholds for a patient may be accomplished in a number of different ways. In general, however, stimulation generator 60 of IMD 12 may be controlled to ramp stimulation intensity for stimulation delivered by different combinations of electrodes, e.g. electrodes 48A-Q on leads 14 and/or 15 from, e.g. zero or another baseline level of intensity up until patient 16 indicates a threshold has been reached. For example, patient 16 may indicate verbally to a clinician that the patient is perceiving the stimulation, experiencing parasthesia, or even pain, or the patient may employ patient programmer 28 or another device to indicate the stimulation intensity at which the threshold is reached. Thresholds may be determined for different individual or combinations of electrodes iteratively or with some simultaneity. In any event, different thresholds for patient 16 may be determined and recorded.

In one example, clinician programmer 26 may be employed to test different stimulation intensities of stimulation delivered by stimulation generator 60 to patient 16. In one example, the stimulation intensities associated with different stimulation thresholds may be determined while patient 16 does not perceive any symptoms from a chronic condition. These stimulation thresholds for one or more electrodes may be associated with prophylactic stimulation modes and stored in memory 52 of IMD 12 and/or memory 55 of programmer 26. In this manner, in one example, the first set of stimulation thresholds associated with patient perception in the absence of any symptoms of a chronic condition may be determined (100). Additionally, stimulation intensities associated with different stimulation thresholds may be determined while patient 16 currently perceives the effect or effects of one or more symptoms of the chronic condition. In one example, alternately, stimulation intensities associated with different stimulation thresholds may be determined without symptoms in effect but based on expected changes in sensitivity or on previously observed effects while patient 16 is symptomatic. These stimulation thresholds for one or more electrodes may be associated with abortive stimulation modes and stored in memory 52 of IMD 12 and/or memory 55 of programmer 26. In this manner, in one example, the second set of stimulation thresholds associated with patient perception while a symptom of the chronic condition is occurring may be determined (102). Specific programming techniques for determining one or more stimulation thresholds are described in more detail in a U.S. Provisional Application No. 61/480,864, filed Apr. 29, 2011, and U.S. Patent Application Publication No. 2012/0277621 by Gerber et al., filed Apr. 26, 2012 and entitled "DETERMINING NERVE LOCATION RELATIVE TO ELECTRODES," which claims the benefit of U.S. Provisional Application No. 61/481,864, the entire contents of both of which are incorporated herein by reference.

With respect to determining stimulation thresholds, whether a first set, second set, or additional sets, patient 16 may, in some examples, be allowed to test and determine stimulation parameters, including thresholds at a number of different times. For example, patient 16 may test and determine abortive therapy parameters including thresholds the next time the patient is symptomatic after an initial programming session with a clinician, so that the determination can be made when symptoms occur. It may also be possible to repeat the determination of thresholds to establish a range of acceptable levels across multiple symptomatic episodes or to establish levels for different symptom modalities or severities.

In addition to determining a first set of stimulation thresholds associated with patient perception in the absence of any symptoms of a chronic condition (100) and determining a second set of stimulation thresholds associated with patient perception while a symptom of the chronic condition is occurring (102), the example method of FIG. 6 also includes delivering prophylactic electrical stimulation to a cranial nerve based on a first range of stimulation thresholds associated with patient perception in the absence of any symptoms of a chronic condition (104), delivering abortive electrical stimulation to the cranial nerve based on a second range of stimulation thresholds associated with patient perception while a symptom of the chronic condition is occurring (106). Regardless of the particular method by which the first and second range of stimulation thresholds are determined for patient 16, processor 50 of IMD 12, or a processor or another component of another device communicatively connected to IMD 12, may employ the stimulation thresholds to control stimulation generator 60 to deliver prophylactic and abortive stimulation to the patient via different combinations of electrodes, e.g. electrodes 90A-90H on lead 88 illustrated in FIG. 7.

In one example, processor 50 controls stimulation generator 60 to deliver prophylactic electrical stimulation to one or more occipital nerves of patient 16 via one or more electrodes based on the first range of stimulation thresholds associated with perception of patient 16 in the absence of any symptoms of a chronic condition (104). The prophylactic stimulation delivered by IMD 12 to patient 16 is configured to inhibit onset of a symptom of the chronic condition of the patient, e.g. inhibit onset of pain associated with a migraine headache. For example, processor 50 may control stimulation generator 60 to deliver prophylactic stimulation to patient 16 according to a set of stimulation parameters defined based on the first range of stimulation thresholds associated with perception of patient 16 in the absence of any symptoms of the chronic condition. The stimulation parameters according to which processor 50 controls stimulation generator 60 to deliver prophylactic stimulation may be, in one example, stored in memory 52 of IMD 12. In one example, the prophylactic stimulation parameters may be embodied in a stimulation program or group of programs stored in memory 52 of IMD 12, or, in the memory of another device communicatively connected to IMD 12, e.g. memory 55 of clinician programmer 26.

In one example, processor 50 may control stimulation generator 60 to deliver prophylactic stimulation to patient 16 including a stimulation intensity within the first range of stimulation thresholds. As described above, defining ranges of stimulation thresholds, e.g. a usability range for different individual electrodes or combinations of electrodes by which stimulation will be delivered to patient 16 by IMD 12 may assist in programming IMD 12 by narrowing the range of possible stimulation intensities that may produce efficacious stimulation therapy to the patient. For example, by defining a usability range between a perception and a pain threshold of patient 16 for, e.g. a particular combination of electrodes 48A-Q on leads 14 and/or 15, stimulation intensities within the usability range may generally be high enough to produce perceivable effects but not too high so as to produce undesirable side effects, such as pain. Because prophylactic stimulation may be delivered by IMD 12 to patient 16 chronically, the intensity of prophylactic stimulation may be selected toward the lower end of the first range of stimulation thresholds for patient 16 in order to increase patient comfort by not chronically delivering a high intensity stimulation to the patient and to conserve energy of power source 54 of IMD 12. Regardless of where within the first range of stimulation thresholds the stimulation intensity by which stimulation generator 60 delivers prophylactic stimulation therapy to patient 16, the intensity, and other stimulation parameters such as pulse width, frequency, and electrode combination, may be selected to balance the desired effects of prophylactic stimulation, including, e.g., maintaining patient comfort and conserving energy of power source 54, while still functioning to inhibit onset of a symptom of the chronic condition of the patient, e.g. inhibit onset of pain associated with a migraine headache.

In addition to delivering prophylactic electrical stimulation (104), IMD 12, and, in particular, stimulation generator 60 may be configured or controlled, e.g. by processor 50 to delivering abortive electrical stimulation to the occipital nerve(s) of patient 16 based on the second range of stimulation thresholds associated with perception of patient 16 while a symptom of the chronic condition is occurring (106), e.g. while the patient is feeling pain from a migraine headache. The abortive stimulation delivered by IMD 12 to patient 16 is configured to reduce an effect of a symptom of the chronic condition, e.g. reduce the pain caused by the migraine. For example, processor 50 may control stimulation generator 60 to deliver abortive stimulation to patient 16 according to a set of stimulation parameters defined based on the second range of stimulation thresholds associated with perception of patient 16 while the patient is feeling pain from a migraine headache. The stimulation parameters according to which processor 50 controls stimulation generator 60 to deliver abortive stimulation may be, in one example, stored in memory 52 of IMD 12. In one example, the abortive stimulation parameters may be embodied in a stimulation program or group of programs stored in memory 52 of IMD 12, or, in the memory of another device communicatively connected to IMD 12, e.g. memory 55 of clinician programmer 26.

In one example, processor 50 may control stimulation generator 60 to deliver abortive stimulation to patient 16 including a stimulation intensity within the second range of stimulation thresholds. In one example, the second range of thresholds may correspond to a usability range associated with perception of patient 16 while a symptom of the chronic condition is occurring, e.g. while the patient is feeling pain from a migraine headache. By defining a usability range between, e.g. a perception and a pain threshold of patient 16 for a particular combination of, e.g. electrodes 48A-Q on leads 14 and/or 15, stimulation intensities within the usability range may generally be high enough to produce perceivable effects but not too high so as to produce undesirable side effects, such as pain. Because abortive stimulation may be delivered by IMD 12 to patient 16 periodically and for relatively short periods of time, the intensity of abortive stimulation may be selected toward the higher end of the second range of stimulation thresholds for patient 16 in order to further reduce the perceivable effects of the symptom(s) of the condition the patient is or will be experiencing. Regardless of where within the second range of stimulation thresholds the stimulation intensity by which stimulation generator 60 delivers abortive stimulation therapy to patient 16, the intensity, and other stimulation parameters such as pulse width, frequency, and electrode combination, may be selected to increase the primary desired effects of abortive stimulation, e.g., of reducing the effect of symptoms of the chronic condition of patient 16. Because the effects of some conditions may be relatively severe, abortive stimulation may be delivered at intensity levels that sacrifice objectives such as patient discomfort from the stimulation and/or energy conservation in an attempt to reduce the effects of the symptom(s) as much as is possible or practical.

As explained above, examples according to this disclosure include a stimulation generator, e.g. stimulation generator 60 delivering prophylactic electrical stimulation to one or more occipital nerves of patient 16 via one or more electrodes based on a first range of stimulation thresholds associated with perception of patient 16 in the absence of any symptoms of a chronic condition and delivering abortive stimulation to patient 16 including a stimulation intensity within the second range of stimulation thresholds. In some examples, the first range of stimulation thresholds and the second range of stimulation thresholds are mutually exclusive such that neither range includes stimulation intensity values included in the other range. In other examples, however, the first range of stimulation thresholds and the second range of stimulation thresholds may partially overlap such that some stimulation intensity values in the first range are also in the second range. In some examples, the first range of stimulation thresholds and the second range of stimulation thresholds may include the same stimulation intensity values.

In one example, delivering the abortive stimulation (106) to patient 16 may include reducing the stimulation intensity of the prophylactic stimulation from within the first range of stimulation thresholds associated with patient perception in the absence of any symptoms of the chronic condition to within the second range of stimulation thresholds associated with patient perception while a symptom of the chronic condition is occurring. As explained above, some patients with some conditions exhibit a particular change in sensitivities to external stimuli from before symptoms of the condition occur to the onset and through the duration of a symptomatic episode of the condition. For example, some migraine patients become hypersensitive to external stimuli during a migraine attack. In such cases, the electrical stimulation threshold and usability range from low to high thresholds of patient 16 may shift generally to lower intensities while patient 16 is experiencing an effect or multiple effects, e.g. pain from the migraine. Thus, for such patients, prophylactic electrical stimulation may be delivered by IMD 12 at a higher intensity level than abortive stimulation. The difference between prophylactic stimulation and abortive stimulation delivered by IMD 12 to patient 16 may include stimulation parameters other than intensity, including, e.g., employing different electrodes or frequencies or targeting different locations, e.g. different nerves between the two stimulation modes.

In some examples, abortive stimulation delivered by IMD 12 to patient 16 may configured, e.g. as to stimulation intensity, electrode combination, and other stimulation parameters, based on effects/side effects that may be tolerable for short durations (during onset of symptoms) but that are not tolerable chronically. For example, muscle contractions, low levels of discomfort, superfluous areas of paresthesia, or other things may be tolerable for relatively short periods of abortive stimulation, e.g. hours, but not longer periods of prophylactic stimulation, e.g. days, weeks, and months. Additionally, abortive stimulation delivered by IMD 12 may include stimulation parameter settings which would be unsustainable for long durations due to, e.g. power constraints of power source 54 of IMD 12. For example, IMD 12 may deliver abortive stimulation employing a higher number of electrodes (and thus high energy levels) for short periods that would, if used chronically, cause power source 54 to prematurely drain or cause unacceptable recharge intervals.

In some examples of the method of FIG. 6, abortive stimulation is delivered to patient 16 in response to anticipating onset of one or more symptoms of the condition of the patient. In one example, anticipating the onset of symptoms includes receiving an indication that patient 16 anticipates the onset of the symptoms. For example, patient 16 may interact with patient programmer 28, or during a programming session, e.g., with clinician programmer 26 to indicate that the patient anticipates the onset of one or more symptoms sometime in the future. In one example, patient 16 interacts with a user interface of patient programmer 28 to indicate to IMD 12 that the patient anticipates the onset of pain from a migraine headache sometime in the future. In response to the anticipation of the onset of the migraine, IMD 12, and, in particular, processor 50 may control stimulation generator 60 to deliver abortive stimulation to patient 16 upon receiving the indication from the patient or at sometime after the patient indicates the onset of the headache is anticipated.

For some patients, a migraine may present with one or more of four symptomatic phases associated with migraine attacks, including the prodrome, which occurs hours or days before the headache, the aura, which more immediately precedes the headache, the pain phase, also known as headache phase, and the postdrome. The phases experienced and the symptoms experienced during each phase can vary from patient to patient and from one migraine attack to another for the same patient. Prodromal symptoms occur in approximately 40-60% of patients with migraines. This phase may consist of some symptom experienced by the patient in advance of the onset of the migraine attack. Prodromal symptoms include, e.g. altered mood, irritability, depression or euphoria, fatigue, yawning, excessive sleepiness, food cravings, muscle stiffness, hot ears, constipation or diarrhea, increased urination, and other visceral symptoms. These symptoms usually precede the headache phase of the migraine attack by several hours or days, and experience may teach the patient how to detect that a migraine attack is near. For the 20-30% of migraine sufferers who experience migraine with aura, this phase of a migraine attack includes focal neurological phenomena that precede or accompany the attack. The aura may begin gradually over 5 to 20 minutes and last fewer than 60 minutes. The headache phase of the migraine attack usually begins within 60 minutes of the end of the aura phase, but it is sometimes delayed up to several hours, and it can be missing entirely. The pain may also begin before the aura has completely subsided. Symptoms of migraine aura can be sensory or motor in nature.

In some examples according to this disclosure, patient 16 may anticipate the onset of a migraine attack based on symptoms associated with one or both of the prodrome or aura of the migraine. In such cases, processor 50 of IMD 12, or a processor or another component of another device communicatively connected to IMD 12 may control stimulation generator 60 to deliver the abortive stimulation to patient 16 during the prodrome or the aura phase of the migraine.

In some examples according to this disclosure, delivering abortive electrical stimulation (106) may include delivering the abortive stimulation in multiple phases. For example, a first phase of abortive stimulation may be delivered by IMD 12 during one of the prodrome or aura phase of a migraine attack experienced by patient 16 and a second phase of abortive stimulation may be delivered by IMD 12 during the pain phase. More generally, in one example, delivering the abortive stimulation to patient 16 includes delivering a first abortive stimulation after the onset of a symptom of the patient's condition is anticipated and delivering a second abortive stimulation while a symptom of the chronic condition is occurring.

In one example, stimulation generator 60 delivers prophylactic stimulation to patient 16 when the patient anticipates the onset of a migraine headache based on symptoms occurring during the prodromal or aura phase of a migraine attack. For example, patient 16 may experience an altered mood, irritability, depression or euphoria, fatigue, yawning, excessive sleepiness, food cravings, muscle stiffness, hot ears, constipation or diarrhea, increased urination, and other visceral symptoms associated with the prodrome of a migraine attack and may indicate the anticipation of the attack by interacting with patient programmer 28. Upon receiving the indication of patient 16 anticipating the migraine attack, patient programmer 28 may communicate with IMD 12 via telemetry modules 56 and 57 of IMD 12 and programmer 28, respectively. Processor 50 of IMD 12 may control stimulation generator 60 to switch from delivering prophylactic stimulation to delivering a first phase of abortive stimulation during the prodrome and/or aura phases of the migraine attack of patient 16. While processor 50 controls stimulation generator 60 to deliver the first phase of abortive stimulation, patient 16 may indicate when the pain phase of the attack begins, after which processor 50 of IMD 12 may control stimulation generator 60 to switch from delivering the first phase of abortive stimulation to delivering a second phase of abortive stimulation throughout the duration of the migraine attack of patient 16. In one example, patient 16 may be able to select, for each of the first and second abortive phases, between different abortive stimulation programs based upon patient preferences, current symptoms, or activities. For example, patient 16 may employ patient programmer 28 to select different abortive stimulation programs via a user interface for first and second abortive stimulation phases, according to which IMD 12 may deliver the stimulation to the patient in the different phases.

In one example, processor 50 may control stimulation generator 60 to deliver the first and the second phases of abortive stimulation to patient 16 according to a set of stimulation parameters defined based on the second range of stimulation thresholds associated with perception of patient 16 while the patient is feeling pain from a migraine headache. The stimulation parameters according to which processor 50 controls stimulation generator 60 to deliver the first and the second phases of abortive stimulation may be, in one example, stored in memory 52 of IMD 12. In one example, the first and the second phase abortive stimulation parameters may be embodied in a stimulation program or group of programs stored in memory 52 of IMD 12, or, in the memory of another device communicatively connected to IMD 12, e.g. memory 55 of clinician programmer 26.

In one example, processor 50 may control stimulation generator 60 to deliver the first and the second phases of abortive stimulation to patient 16 including a stimulation intensity in each of the phases that is within the second range of stimulation thresholds associated with patient perception while a symptom of a migraine is occurring. In another example, stimulation generator 60 delivers stimulation to patient 16 in the first phase of abortive stimulation at an intensity within the first range of stimulation thresholds associated with patient perception in the absence of any symptoms of a migraine headache and delivers stimulation in the second phase of abortive stimulation at an intensity within the second range of stimulation thresholds associated with patient perception while a symptom of a migraine is occurring. In another example, the second phase of abortive stimulation may be delivered by IMD 12 reducing the stimulation intensity of the first phase of abortive stimulation from within a first range of stimulation thresholds that is associated with perception of patient 16 during the onset of a symptom of a migraine to within a second range of stimulation thresholds associated with patient perception after the intensity level of the symptom has increased above the level during the onset of the symptom. In some patients, onset of symptoms may occur before hypersensitivity to external stimuli. In such cases, the highest intensity of stimulation delivered in prophylactic or abortive modes may be used in the first abortive stimulation phase in an attempt to prevent or abort onset. If this fails, and the patient becomes sensitized, lower levels may then be needed in the second phase of abortive stimulation. In view of the foregoing variations, in one example, the stimulation intensity of the first phase of abortive stimulation delivered by IMD 12 to patient 16 may be greater than the stimulation intensity of the second phase of abortive stimulation. In another example, the stimulation intensity of the first phase of abortive stimulation delivered by IMD 12 to patient 16 may be less than the stimulation intensity of the second phase of abortive stimulation. Additionally, one or both of the first and the second phases of abortive stimulation may be delivered by IMD 12 to patient 16 at a stimulation intensity that is greater than or less than the intensity of prophylactic stimulation.

In one example, processor 50 may control stimulation generator 60 to deliver abortive stimulation to patient 16 including adding one or more electrodes to an electrode combination by which prophylactic stimulation is delivered and/or deliver stimulation to additional locations, e.g. additional target nerves. For example, processor 50 may control stimulation generator 60 to deliver abortive stimulation by adding one or more electrodes to the combination of, e.g. electrodes 48A-Q employed for prophylactic stimulation delivered by IMD 12. In one example, processor 50 may cluster electrodes or electrode combinations to the combination of electrodes 48A-Q used for prophylactic stimulation during delivery of abortive stimulation to patient 16. Electrode clustering is described in more detail below and in U.S. Patent Application Publication No. 2012/0277621 by Gerber et al., filed Apr. 26, 2012 and entitled "DETERMINING NERVE LOCATION RELATIVE TO ELECTRODES," which claims the benefit of U.S. Provisional Application No. 61/480,887, the entire contents of both of which are incorporated herein by reference. However, in general, processor 50 may cluster one or more of electrodes 48A-Q or combinations thereof based on stimulation threshold(s) of the electrodes, e.g. based on similar upper and/or lower threshold or similar usability ranges.

In one example, which may include adding electrodes, processor 50 may control stimulation generator 60 to deliver abortive stimulation by delivering stimulation to one or more additional locations, e.g. additional target nerves than targeted during prophylactic stimulation. For example, processor 50 may target the left occipital nerve via electrodes on lead 14 during prophylactic stimulation and control stimulation generator 60 to deliver stimulation to the left occipital nerve and to a supraorbital nerve via additional electrodes (not shown in FIG. 1A or 1B) during abortive stimulation. In another example, processor 50 may target the left occipital nerve via electrodes on lead 14 during prophylactic stimulation and control stimulation generator 60 to deliver stimulation to the left occipital nerve via electrodes on lead 14 and the right occipital nerve via electrodes on lead 15 during abortive stimulation.

As noted above, some patients are hypersensitive to external stimuli during a symptomatic attack of the condition of the patient. For example, some migraine patients become hypersensitive to external stimuli during a migraine attack. In such cases, the electrical stimulation delivered to the patient in an abortive stimulation mode while patient 16 is experiencing an effect or multiple effects, e.g. pain from the migraine may include a lower intensity than the prophylactic stimulation delivered to the patient. These conditions may occur regardless of particular stimulation thresholds for the patient and the prophylactic and abortive stimulation modes may be delivered without necessarily determining or basing the stimulation on such thresholds. Thus, in one example according to this disclosure, processor 50 of IMD 12 may be configured to control stimulation generator 60 to deliver prophylactic electrical stimulation to target stimulation sites 18 and 19 via one or more electrodes 48A-Q on leads 14 and/15 in order to inhibit onset of a symptom of a chronic condition and to deliver abortive electrical stimulation to target stimulation sites 18 and 19 via combinations of electrodes 48A-Q on leads 14 and/or 15 in order to reduce an effect of a symptom of the chronic condition. In such examples, processor 50 may control stimulation generator 60 to deliver the prophylactic stimulation at a stimulation intensity that is greater than the stimulation intensity at which IMD 12 delivers the abortive stimulation, e.g. according to stimulation parameters including intensity stored in one or more programs on memory 52 as described in more detail below. Reducing the stimulation intensity during the abortive stimulation mode may act to reduce the risk of increasing the adverse effects of a symptomatic episode of a condition of patient 16, e.g. reduce the risk of increasing pain from a migraine attack due the patient's hypersensitivity to the stimulation during the migraine attack. In another example, processor 50 may control stimulation generator 60 to deliver abortive stimulation to patient 16 by switching to different electrodes than employed for prophylactic stimulation, which electrodes may have lower stimulation thresholds but larger usability ranges.

In some examples of delivering prophylactic and abortive stimulation according to this disclosure, stimulation thresholds for a patient may be employed to cluster multiple individual electrodes or electrode combinations into a single stimulation program defining delivery of stimulation therapy to increase utilization of resources that may provide efficacious results to a patient. Clustering electrodes may be useful in situations where device configuration limits the number or type of stimulation programs that may be employed. For example, in some implementations of an implantable neurostimulator, the number of distinct stimulation programs that may define stimulation delivered to a patient may be limited to a number that is less than the number of different efficacious electrode combinations by which stimulation may be delivered to a particular patient. In such circumstances, clustering multiple electrode combinations in a single program may increase resource utilization and may ultimately improve the efficacy of the therapy delivered to the patient.

Clustering may include determining if one or more electrodes have similar characteristics that allow for stimulation to be provided to a nerve using the electrodes configured to deliver stimulation according to the same stimulation program, e.g. according to the same stimulation parameters including, e.g. intensity, pulse width, and frequency. In some examples, electrodes may be clustered based on one or more stimulation thresholds associated with each of the electrodes or combinations thereof for a particular patient. For example, electrodes with similar paresthesia thresholds may be clustered together. In another example, electrodes or combinations of electrodes with similar usability ranges, e.g. similar low and/or high thresholds and similar ranges of stimulation intensities may be clustered together.

In examples according to this disclosure, electrodes or electrode combinations may be clustered for one or both of the prophylactic and the abortive stimulation modes. For example, processor 50 may control stimulation generator 50 to deliver stimulation via two or more individual electrodes or electrode combinations in a prophylactic stimulation mode by clustering the electrodes or combinations based on stimulation thresholds associated with perception of patient 16 in the absence of any symptoms of a chronic condition of the patient. In one example, in addition to or independent of clustering in the prophylactic mode, processor 50 may control stimulation generator 50 to deliver stimulation via two or more individual electrodes or electrode combinations in an abortive stimulation mode by clustering the electrodes or combinations based on stimulation thresholds associated with perception of patient 16 while a symptom of the chronic condition is occurring, e.g. while patient 16 feels pain from a migraine headache. Clustering individual electrodes or electrode combinations by which electrical stimulation is delivered to a patient is described in more detail in U.S. Patent Application Publication No. 2012/0277621 by Gerber et al., filed Apr. 26, 2012 and entitled "DETERMINING NERVE LOCATION RELATIVE TO ELECTRODES," which claims the benefit of U.S. Provisional Application No. 61/480,887, the entire contents of both of which are incorporated herein by reference Techniques described in this disclosure associated with control electronics of an IMD or external device, such as an external programmer may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform various functions, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable storage media.

Various examples have been described. These and other examples are within the scope of the following claims.

The invention claimed is:

1. A method comprising:
    delivering prophylactic electrical stimulation to a cranial nerve at a first stimulation intensity within a first range of stimulation intensity thresholds determined based on patient perception in the absence of any symptoms of a chronic condition, wherein the prophylactic stimulation is configured to inhibit onset of a symptom of the chronic condition; and
    delivering abortive electrical stimulation to the cranial nerve at a second stimulation intensity within a second range of stimulation intensity thresholds determined based on patient perception while a symptom of the chronic condition is occurring, wherein the abortive stimulation is configured to reduce an effect of a symptom of the chronic condition.

2. The method of claim 1, wherein the first range of stimulation intensity thresholds comprises a range from a first low stimulation intensity threshold determined based on patient perception to a first high stimulation intensity threshold determined based on patient perception, and wherein the first low stimulation intensity threshold comprises at least one of a first perception threshold or a first paresthesia threshold and the first high stimulation threshold comprises at least one of a first muscle recruitment threshold, a first discomfort threshold, or a first pain threshold.

3. The method of claim 2, wherein the second range of stimulation intensity thresholds comprises a range from a second low stimulation intensity threshold determined based on patient perception to a second high stimulation intensity threshold determined based on patient perception, and wherein the second low stimulation intensity threshold comprises at least one of a second perception threshold or a second paresthesia threshold and the second high stimulation intensity threshold comprises at least one of a second muscle recruitment threshold, a second discomfort threshold, or a second pain threshold.

4. The method of claim 1, wherein delivering the abortive stimulation comprises reducing a stimulation intensity of the prophylactic stimulation from a stimulation intensity within the first range of stimulation intensity thresholds to a stimulation intensity within the second range of stimulation intensity thresholds.

5. The method of claim 1, wherein delivering the abortive stimulation comprises:
    delivering a first abortive stimulation after onset of a symptom of the chronic condition is anticipated; and
    delivering a second abortive stimulation while the symptom of the chronic condition is occurring.

6. The method of claim 5, wherein delivering the second abortive stimulation comprises delivering the second abortive stimulation after an intensity level of the symptom has increased above a level during the onset of the symptom.

7. The method of claim 1, further comprising anticipating onset of a symptom of the chronic condition.

8. The method of claim 7, wherein the abortive stimulation is delivered in response to anticipating the onset of the symptom of the chronic condition.

9. The method of claim 1, wherein the first range of stimulation intensity thresholds is different than the second range of stimulation intensity thresholds.

10. The method of claim 1, wherein the first stimulation intensity is greater than the second stimulation intensity.

11. The method of claim 1, wherein the chronic condition is one of migraine headaches, occipital neuralgia or trigeminal neuralgia.

12. The method of claim 1 further comprising:
receiving an indication from the patient of anticipation of the onset of a symptom of the chronic condition; and
in response to receiving the indication, delivering the abortive electrical stimulation.

13. A system comprising:
an implantable electrical stimulation generator; and
a processor configured to control the stimulation generator to deliver prophylactic electrical stimulation to a cranial nerve at a first stimulation intensity within a first range of stimulation intensity thresholds determined based on patient perception in the absence of any symptoms of a chronic condition, and to deliver abortive electrical stimulation to the cranial nerve at a second stimulation intensity within a second range of stimulation intensity thresholds based on patient perception while a symptom of the chronic condition is occurring,
wherein the prophylactic stimulation is configured to inhibit onset of a symptom of the chronic condition, and
wherein the abortive stimulation is configured to reduce an effect of a symptom of the chronic condition.

14. The system of claim 13, wherein the first range of stimulation intensity thresholds comprises a range from a first low stimulation intensity threshold determined based on patient perception to a first high stimulation intensity threshold determined based on patient perception, and wherein the first low stimulation intensity threshold comprises at least one of a first perception threshold or a first paresthesia threshold and the first high stimulation intensity threshold comprises at least one of a first muscle recruitment threshold, a first discomfort threshold, or a first pain threshold.

15. The system of claim 14, wherein the second range of stimulation intensity thresholds comprises a range from a second low stimulation intensity threshold determined based on patient perception to a second high stimulation intensity threshold determined based on patient perception, and wherein the second low stimulation intensity threshold comprises at least one of a second perception threshold or a second paresthesia threshold and the second high stimulation intensity threshold comprises at least one of a second muscle recruitment threshold, a second discomfort threshold, or a second pain threshold.

16. The system of claim 13, wherein the processor is configured to control the stimulation generator to deliver the abortive stimulation at least by reducing a stimulation intensity of the prophylactic stimulation from within the first range of stimulation intensity thresholds to within the second range of stimulation intensity thresholds.

17. The system of claim 13, wherein the processor is configured to control the stimulation generator to deliver a first abortive stimulation after onset of a symptom of the chronic condition is anticipated and deliver a second abortive stimulation while the symptom of the chronic condition is occurring.

18. The system of claim 17, wherein the processor is configured to control the stimulation generator to deliver the second abortive stimulation after an intensity level of the symptom has increased above a level during the onset of the symptom.

19. The system of claim 13, wherein the processor is configured to receive an indication of anticipating onset of a symptom of the chronic condition.

20. The system of claim 19, wherein the processor is configured to control the stimulation generator to deliver the abortive stimulation in response to receiving the indication of anticipating the onset of the symptom of the chronic condition.

21. The system of claim 13, wherein the implantable electrical stimulation generator and the processor reside within a housing of an implantable medical device.

22. The system of claim 13, further comprising an external programmer comprising the processor.

23. The system of claim 13, wherein the first range of stimulation intensity thresholds is different than the second range of stimulation intensity thresholds.

24. The system of claim 13, wherein the first stimulation intensity is greater than the second stimulation intensity.

25. The system of claim 13, wherein the chronic condition is one of migraine headaches, occipital neuralgia or trigeminal neuralgia.

26. The system of claim 13, wherein the processor is further configured to deliver the abortive electrical stimulation in response to receiving an indication from the patient of anticipation of the onset of a symptom of the chronic condition.

27. A computer-readable storage medium comprising instructions for causing a programmable processor to:
deliver prophylactic electrical stimulation to a cranial nerve at a first stimulation intensity within a first range of stimulation intensity thresholds determined based on patient perception in the absence of any symptoms of a chronic condition, wherein the prophylactic stimulation is configured to inhibit onset of a symptom of the chronic condition; and
deliver abortive electrical stimulation to the cranial nerve at a second stimulation intensity within a second range of stimulation intensity thresholds determined based on patient perception while a symptom of the chronic condition is occurring, wherein the abortive stimulation is configured to reduce an effect of a symptom of the chronic condition.

\* \* \* \* \*